(12) United States Patent
Van de Capelle et al.

(10) Patent No.: US 6,483,607 B1
(45) Date of Patent: Nov. 19, 2002

(54) METHOD AND DEVICE FOR DETERMINING THE COLOR APPEARANCE OF COLOR OVERPRINTS

(75) Inventors: Jean-Pierre Van de Capelle, Merelbeke; Baldewin Meireson, Zingem, both of (BE)

(73) Assignee: Detrix N. V., Wijnaarde (BE)

( * ) Notice: Subject to any disclaimer, the term of this patent is extended or adjusted under 35 U.S.C. 154(b) by 0 days.

(21) Appl. No.: 09/361,435

(22) Filed: Jul. 26, 1999

Related U.S. Application Data

(63) Continuation-in-part of application No. 08/824,689, filed on Apr. 8, 1997, now Pat. No. 5,933,578.

(51) Int. Cl.$^7$ ................................................. G06F 13/00

(52) U.S. Cl. ........................ 358/1.9; 358/518; 358/525

(58) Field of Search .................... 358/1.9, 500, 501, 358/504, 518, 525, 534; 101/23

(56) References Cited

U.S. PATENT DOCUMENTS 5,530,656 A * 6/1996 Six ............................ 101/365

OTHER PUBLICATIONS

"A model for Color Prediction of Halftoned Samples Incorporating Light Scattering and Ink Spreading", Patrick Emmel, Roger David Hersch, Seventh Color Imaging Conference, Nov. 16–19, 1999; pp. 173–182.

"A new method for characterizing output devices and its fit into ICC and HIFI color work flows", Jean–Pierre van de Capelle and Baldewin Meireson, Fifth Color Imaging Conference, Nov. 17–20, 1997; pp. 66–69.

* cited by examiner

*Primary Examiner*—Mark Wallerson
(74) *Attorney, Agent, or Firm*—Dov Rosenfeld; Inventek

(57) ABSTRACT

A method and apparatus for determining a small number of parameters that spectrally characterize colorants by a small number of parameters and for using such colorant parameters to accurately predict the spectral reflection or transmission characteristics of such colorants when deposited on top of one another, either on an opaque, transparent or semitransparent carrier of a particular type, each colorant deposited with a certain coverage percentage, for example, dot percentage in the case of offset printing, the colorant parameters of any colorant being substantially independent of the color of the substrate and including dependency on the colorants deposited before and after. The method involves making measurements of sets prints of varying coverage percentages of a colorant on a number of backgrounds, and solving the resulting set of equations for the colorant. Colorants that are defined by a recipe of basic colorants can be characterized from measurements on prints of the basic colorants.

34 Claims, 7 Drawing Sheets

METHOD AND DEVICE FOR DETERMINING THE COLOR APPEARANCE OF COLOR OVERPRINTS

RELATED APPLICATION

The present application is a continuation-in-part of U.S. patent application Ser. No. 08/824,689, filed Apr. 8, 1997 now U.S. Pat. No. 5,933,578, and entitled METHOD AND DEVICE FOR DETERMINING THE COLOR APPEARANCE OF COLOR OVERPRINTS (the "Parent Invention"), the priority of which is hereby claimed pursuant to 35 U.S.C. §120, and the entirety of which is incorporated herein by reference.

FIELD OF THE INVENTION

The present invention relates to computerized color graphics, color reproduction, and electronic printing systems. In particular, the present invention relates to a method and apparatus for characterizing colorants such as inks and predicting the color appearance of placing one or more colorant layers on top of a substrate such as paper or film as occurs, for example, in printing a page and photography.

BACKGROUND OF THE INVENTION

Computerized color graphics systems and electronic printing systems are known in the art. Typically, they enable a user to produce a color image (any visual two-dimensional pattern including text, graphic line art, continuous tone images, etc.), and from that image to produce a picture which can be printed via a color reproduction system, for example, by producing color separation plates for offset printing. There has been much effort in the past to develop ways to accurately predict or simulate the appearance of such images when printed on a substrate, for example paper or film, using a number of colorants, such as inks, the prediction carried out without actually printing the images.

Printing may be carried out using halftoning, also called screening, which is the process of creating the illusion of a continuous tone ("CT," "contone") image using an output (e.g., printing) device capable only of binary output (ink deposited or not deposited at any location on a substrate). For color printing, several images ("separations") are produced in the primary colorants (typically inks) used to print in color, and printed over each other in a press. For typical four color printing, four images are produced in cyan ("C"), magenta ("M"), yellow ("Y") and black ("K"), and each of these images are halftoned. Usually, digital halftoning is used together with an imagesetter, laser printer, ink jet printer, digital film recorder, or other recorder output device.

It is desirable to be able to calculate accurately how a picture will look when one prints an image, including a halftoned continuous tone color image, with a certain technique on a certain substrate using a certain set of colorants (e.g., inks). A method of predicting the color appearance can be used for example to display a simulation of the color appearance on a computer display, or to print a simulation of the color appearance on a more easily accessible and cheaper printer as a proof of what is to be printed finally in production.

It is desirable to do this for both reflection printing on an opaque substrate, and transmission imaging on a transparent substrate.

By accurately calculating we mean a maximum deviation between predicted color and actual color of the order of 5 CIELAB Delta E units, and an average deviation of about 2 CIELAB Delta E units.

PRIOR ART METHODS

Various methods are known for calculating the color resulting from superimposing a set of colorant layers on a substrate. These methods can be divided in two groups. The first group are characterized by requiring printing and measuring a relatively large number of overprints of the colorants. That is, this group includes methods that for a particular set of colorants, a particular printing technique (e.g., offset printing on a particular imagesetter), a particular substrate type (e.g., paper, or film for a photographic transparency or print, textile, sheet of plastic, etc.), a particular substrate color (e.g., the color of the paper, or of the transparent film in the case of a transparency, or of the textile, or of the plastic sheet, etc.) and a particular order of printing the colorants, involve printing a relatively large number of overprints of the colorants in the set, for example as patches. These patches are measured with a spectrophotometer or calorimeter and the measurements are used to calculate any overprint of colorants in the set using mathematical techniques, for example, interpolation. If carried out well and carefully, these methods can lead to accurate results. Modem color management techniques such as COLORSYNC™ (Apple Computer, Inc., Cupertino, Calif.) and the methods promoted by the International Color Consortium (ICC, see http://www.color.org) use such techniques. While these techniques can produce accurate results, and also work for halftone images, there are several drawbacks with such methods. One is that a large number of color patches of overprints need to be made. For example, the IT8.7.3 chart (American National Standards Institute [ANSI] Committee IT8 for Digital Data Exchange Standards) contains nearly a thousand patches for a four color output. Hence it is very difficult to characterize sets of more than four colorants, for example printing with six or seven colors ("HI-FI" printing including PANTONE® Hexachrome from Pantone, Inc., Carlstadt, N.J.). There also are applications where inks other than cyan, magenta, yellow and black need to be used. Another drawback is that a set of patches will only be useful for accurately calculating overprints using the particular colorants and the particular colorant printing order used in the patches. Changing one colorant in the colorant set or changing the order of overprinting typically requires redoing the whole job of printing the set of patches.

An additional problem occurs when using such characterizations with more than four inks in a typical modem color management workflow, such as the ICC workflow. The ICC standard uses look up tables and interpolation to predict the CIELAB values of a particular output device. The number of nodes in these lookup tables increases exponentially with the number of inks, and the amount of computer resources becomes too high to be feasible.

Also included in this first group of known methods are those that use the well known Neugebauer equations to predict the color of an overprint of colorants, and their derivative based on Yule-Nielsen and spectral Neugebauer equations (See H. E. J. Neugebauer: "Die theoretischen Grundlagen des Mehrfarbenbuchdrucks", *Zeitschrift fur wissenschaftliche Photographie, Photophysik und Photochemie*, Band 36, Heft 4, April 1937; J. S. Arney, C. D. Arney:" Modeling the Yule-Nielsen Halftone effect," Journal of imaging science and technology, vol. 40, No. 3, pp. 233–238, June 1996; R. Rolleston and R. Balasubramanian: "Accuracy of Various Types of Neugebauer Model", *IS&T and SID's Color Imaging Conference: Transforms and Transportability of Color*, pp. 32–37, 1993). These Neugebauer-like models still need the knowledge of the color of the overprints of the primary inks, so still requires measurements overprint combinations of the colorants and the gradation steps of the colorants. Also, Neugebauer equations-based methods are known not to produce accurate results.

A second group of prior art methods are those that determine spectral characterizations of individual colorants that can be used for predicting the color of overprints of so-characterized colorants. These methods, for a fixed substrate and printing technique, involve making one or more printouts of each colorant on one or more substrates, measuring the prints, and out of this data extracting a set of one or more parameters for each colorant that can be used to calculate an overprint of each colorant. These methods thus have the advantage of not requiring producing a large set of overprints. One such prior art method uses the two-parameter Kubelka-Munk method which describes an ink wither by one spectral parameter, $(K/S)(\lambda)$, or by two spectral parameters, scattering $S(\lambda)$ and absorption $\alpha(\lambda)$, where $\lambda$ is the wavelength. See James H. Nobbs: "Kubelka-Munk Theory and the Prediction of Reflectance", *Rev. Prog. Coloration*, Vol. 15, pp. 66–75, 1985.

Determining the two colorant parameters involves measuring the spectrum on a bare substrate and on a black substrate, and solving the resulting equations. There also exist in the literature refinements on the two-parameter Kubelka-Munk theory that incorporate internal reflection, anisotropic scattering and other second order effects. However, these methods are applicable only for full (i.e., 100%) coverage of a layer of ink of a particular thickness, and/or are not applicable for variable ink coverages, for example, halftoning at less than 100% dot percentage. In addition, the colorant parameters they determine are neither substantially independent of the lowest substrate color nor are capable of incorporating dependencies on other ink layers. Thus these parameters are not easily applied to predicting the appearance of sequentially applied inks at less than 100% coverage wherein the substrate with the previously deposited inks may be regarded as a new substrate, with characterizable influence from layer to layer.

In order to so predict the appearance of overprints, it is advantageous to spectrally characterizing colorants by parameters that are substantially invariant for all substrates of the same type, and independent of the substrate color, in that, when there is no interaction between colorant layers, one can treat a substrate with one or more colorant overprints on it as a raw colored substrate of the same type but a different color, that different color dependent on the one or more colorant overprints.

In summary, prior art techniques that are capable of accurately calculating overprints of inks, including rasterized (i.e., halftoned) inks, require making a number of overprints of the colorants, so do include determining spectral parameters of a colorant that spectrally characterize the colorant. Furthermore, prior art techniques that do spectrally characterize the colorants are not applicable to less than 100% coverage, do not produce parameters that are substantially independent of substrate color, and do not produce parameters that can take into account interactions between the colorant layers.

Thus there is a need in the art for a method of characterizing colorants capable of accurately predicting the color of an overprint of the colorants without requiring measurement of overprints of the colorants and capable of predicting the color of overprints of halftones.

The Parent Invention describes such a method for determining and using colorant parameters that are substantially independent on the substrate color. The use of these parameters is described when there is no interaction between the layers. At least two parameters are needed for non-scattering parameters and at least three parameters are needed for scattering colorants. Such colorant parameters also may be used when there is some interaction between the layers of colorants. Parameters in such a case also may be determined that are capable of characterizing some interdependency of the colorants deposited, so that even when there is interaction between layers, one can treat a substrate with one or more colorant overprints on it as a raw colored substrate of the same type. Needed is a more detailed description of how the Parent Invention is applicable to this case of the colorant layers influenced each other. That is, the effect of any colorant being influenced by one or more of the inks printed before or after in an overprint.

Examples of when the effect of a colorant (e.g., ink) may be so dependent on inks earlier printed on which the new ink is to be printed, include phenomena such as "ink trapping" in which an ink is "taken up" less by the substrate when another ink has first been printed onto this substrate. Such a phenomenon could occur, for example, in offset printing. Another case is when the parameters of one or more inks already deposited onto a substrate are influenced on a new ink being deposited on top of these previously deposited inks. A lower ink may "spread" as a result of additional inks deposited on top, so that the area the lower ink covers is increased. This is called "spreading" herein, and might occur, for example, with ink-jet printing. Other examples when one colorant may be dependent on one or more overlying or underlying colorant layers include an ink-re-transfer-like phenomenon which could occur, for example, in dye sublimation printing, and mixing of the inks, which can occur in many printing techniques.

In the cases of "trapping" and "spreading", the perceived ink quantity (halftone coverage percentage) also may change from the amounts laid down because of such interdependencies.

Thus there is a need in the art for a method for characterizing the spectral properties of colorants overprinted at a coverage percentage which may be less than 100%, on a reflective or transmittive substrate, the characterizing being by a small number of colorant parameters that are a function of the coverage percentage and that are substantially invariant to the substrate color for all substrates of a particular substrate type and for a particular printing technique, such colorant parameters capable of substantially incorporate the dependency on the colorants deposited before and after. Also, there still is a need in the art for a method and apparatus for accurately predicting the color of printing a set of colorants at any coverage percentages on a reflective or transmittive substrate, the method not requiring making and measuring overprints of the colorants, and applicable to overprinting where each colorant is laid at less than 100% coverage, for example using halftoning.

SUMMARY OF THE INVENTION

An object of this invention is a method for characterizing the spectral properties of colorants such as inks when printed on a substrate of a particular type by a small number of parameters which are independent of the base substrate color and that can incorporate interaction between other colorants printed on the substrate. A further object of this invention is a method and apparatus which use such characterization for predicting the color of printing a set of colorants such as inks on a substrate. Other objects would be clear from the description below.

These and other objects of the invention are provided for in a method and apparatus for determining a set of colorant parameters that spectrally characterize a colorant in order to predict the color spectrum of an overprint of the colorant deposited using a printing technique at a coverage percentage on a substrate of a substrate type, the set of colorant parameters substantially independent of the base substrate color and capable of incorporating mutual dependencies of the colorant with other colorants deposited on the substrate. For the example of offset printing using halftoning, these colorant parameters are a function of the dot percentage and wavelength.

At least two parameters are determined for characterizing a non scattering colorant, and at least three are determined for a colorant that has scattering properties. When mutual interaction of colorant layers in an overprint is possible, at least six parameters are determined for characterizing a non scattering colorant, and at least eight are determined for a colorant that has scattering properties.

In one aspect of the invention, the method includes making a number of sets of prints of the colorant at a range of coverage percentages on different background colors, for example, different dot percentages for the case of offset printing. To incorporate mutual interaction, more parameters need to be determined, so additional set of prints are made. For example, three sets of prints are made on three backgrounds for non scattering colorants and on four backgrounds for scattering colorants and in addition, if necessary to obtain a sufficient number of sets of prints on different backgrounds to determine the parameters, one or more similar sets of printouts are overprinted with one or more overprinting colorants.

The spectra of the prints, for example, the reflection spectra in the case of offset printing, are measured, and equations in the set of parameters are formed and numerically solved for the parameters. The backgrounds are, in one embodiment, two lightly colored backgrounds, a medium colored background, and, for the case of four sets of prints, a dark colored background and any overprinting is done with a lightly colored colorant. In one implementation for offset printing, the four backgrounds are formed by pre-printing the backgrounds, for example, in the case of the lightly colored background using 25% halftone dots, for the medium dark background, using 50% halftone dots with black ink, and in the case of the dark background used for the case of a colorant that has a scattering component, using 100% black ink, the overprinting happens for instance with a 100% colorant in a second set of prints. For coverage percentages for which prints are not made, interpolation is used to determine the parameters for such colorant coverages.

Some colorants, called derived colorants, can be defined by a recipe of concentrations of basic inks. In another aspect of the invention, the set of colorant parameters of a derived colorant is determined by making measurements on a set of dilutions of each of the basic colorants on several background colors on one or more substrates of the same substrate type, a set of dilutions in this sense possibly including the undiluted basic colorant. The prints that are made of each of the dilutions at different colorant coverages are the same as would be made to determine the colorant parameters of each of the dilutions of the basic colorants. Measurements of the resulting spectra are made. From these, coefficients, for example Kubelka-Munk coefficients are determined for the dilutions at the coverage percentages, and, using interpolation, Kubelka-Munk coefficients are determined for the concentrations specified in the recipe of the derived colorant. Then, using a formula for mixtures of colorants using the coefficients, for example, the Kubelka-Munk theory for mixtures modified for all the printed coverage percentages, the spectra that would result by printing the derived colorant on the different backgrounds at the different coverage percentages are calculated without actually having to print the derived colorant. From these calculated spectra, using steps analogous to the case of determining the spectral parameters directly, the spectral parameters of the derived colorant are determined.

In another aspect of the invention, a method for using the parameters for determining a single overprint of a colorant on a substrate also is disclosed. Using the result that the colorant parameters are substantially independent of substrate color and can incorporate the effects of interdependency with other colorants, a method is disclosed for determining the spectrum of several overprints of several colorants by sequentially applying the method for one colorant. One first determines the coverage percentages 'below' and 'above' each colorant, i.e., for a particular colorant, those on which the colorant is deposited and those deposited over the colorant, and from these percentages, one modifies the colorant parameters and then determines the color of the colorants when deposited sequentially on the background in much the same way as if the colorant parameters were substantially independent of each other (see the Parent Invention). the reflection spectrum of an overprint of the first colorant on the raw substrate. One then treats the resulting print as a new substrate of the same type but a different color (the color given by the first obtained reflection spectrum) and in the same way determines the reflection spectrum of overprinting a second colorant on top of the first. One continues this process until one has determined the reflection spectrum of all the overprints of the several colorants.

Also disclosed is an apparatus for using the colorant parameters to determine the spectrum of overprints on a substrate of a set of colorants at a set of coverage percentages. The apparatus comprises a first memory for storing the spectrum of the substrate, a logic unit with inputs specifying the coverage percentages and a set of outputs which are the values of the colorant parameters (as modified by interaction between the colorant layers) at the coverage percentages. When inter-layer interaction may occur, some dot gain values also are input for a range of coverage percentages. The outputs of the logic unit are coupled to a combiner unit, which also has an input coupled to the first memory. The combiner unit determines the color spectrum of the overprints on the substrate of the set of colorants at the set of coverage percentages. One embodiment of the apparatus described comprises the logic unit being implemented as one or more lookup tables and an arithmetic unit. Another embodiment described comprises the logic unit being implemented as one or more interpolators for determining by interpolation the colorant parameters at the required coverage percentages for each colorant from values of the parameters at a set of fixed values of coverage percentages and an arithmetic unit that incorporates the calculation of the average coverage percentage below and above each colorant and the modification of the colorant parameters by these coverage percentages. The combiner unit is implemented as one or more arithmetic units, each arithmetic unit having an associated background spectrum as an input and a set of colorant parameters at a coverage percentage as another input and determining the spectrum of the overprint of that colorant on a substrate having the associated background spectrum. A parallel implementation is described in which the number of sets of interpolators in the logic unit is the number of colorants and the number of arithmetic units in the combiner unit also is the number of colorants. A serial implementation also is disclosed which is applicable to the case of no interaction between th layers and in which the logic unit comprises a single set of interpolators for a single colorant and the combiner unit comprises a single arithmetic unit for determining a single overprint. The operation of such a serial implementation is that the logic unit and arithmetic unit determine one overprint at a time in sequence, starting with an overprint on the raw substrate, and continuing with the second overprint being on the raw overprint with the first colorant, etc., until all overprints have been determined. After a number of cycles equal to the number of colorant overprints, the output of the arithmetic unit is the spectrum of all the overprints.

Also disclosed is a method and apparatus for simulating the appearance of overprints of a set of colorants on a display using colorant parameters determined according to one or more embodiments of the method of the invention for such determination. One embodiment of the method includes the steps of determining the spectrum of the overprints according to one or more of the above embodiments for determining the spectrum of overprints, and from the spectrum, determining the CIE-XYZ values of the overprint using CIE illuminant-observer weightings, and converting these XYZ values to RGB values to drive a CRT (or LCD, etc.) monitor using matrix multiplication and, in some embodiments, also one-dimensional lookup tables. Another aspect of the method includes using a matrix multiplier, one dimensional lookup tables, a multidimensional lookup table and interpolation for converting the XYZ values to the device dependent color values needed to drive a proof printer. One embodiment of the apparatus includes an apparatus for determining the spectrum of the overprints according to one or more of the above embodiments, and multiplier adders for determining the CIE-XYZ values of the overprint using CIE illuminant-observer weightings, and a matrix multiplier and, in some embodiments, also one dimensional lookup tables to produce RGB values to drive a CRT monitor. Another aspect of the apparatus includes a matrix multiplier, one dimensional lookup tables, a multidimensional lookup table and a multidimensional interpolator for converting the XYZ values to the device dependent color values needed to drive a proof printer.

These and other objects, features, aspects and advantages of the present invention will become more apparent from the following detailed description of preferred embodiments with the accompanying drawings.

DETAILED DESCRIPTION OF THE PREFERRED EMBODIMENTS

Figure 1:
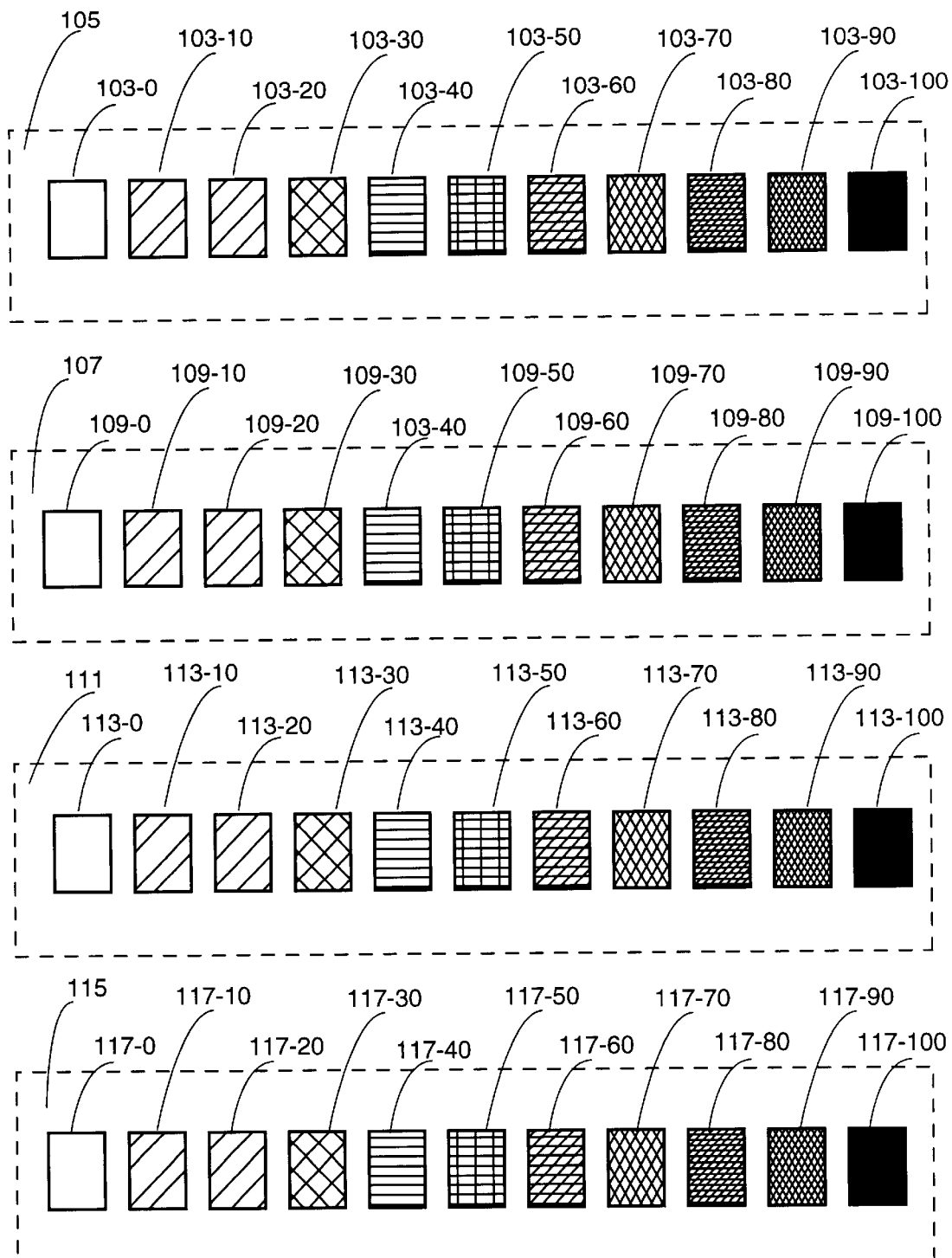
FIG. 1 shows the first set of prints made and measured in order to determine the colorant parameters for the case that includes scattering according to one embodiment of the method of the invention.

A preferred embodiment of the present invention is a method implemented on a computer. The steps of the method are performed by the computer executing a software program.

The Single Colorant Case

The first case considered is characterizing by a small number of spectral parameters the spectral properties of a colorant for printing the colorant with a particular printing technique on a substrate. The Parent Invention described how colorants that are considered non-scattering can be characterized according to one aspect of this invention by two spectral parameters, and how colorants that have scattering properties can be characterized according to another aspect of this invention by three spectral parameters. More than two spectral parameters are necessary for some non-scattering colorants, and more than three spectral parameters are necessary for scattering colorants in the case when the colorants laid under a particular colorant influence the effect of that colorant, and when the colorants laid on top a particular colorant influence the effect of that colorant. In particular, in such a case for instance, eight colorant parameters are needed for a scattering ink, while six colorant parameters are needed when there is no scattering. This invention is not limited to characterizing colorants by any particular maximum number of parameters.

Consider n inks deposited on a substrate, and consider the $i^{th}$ such ink, where i is an index between 1 and n. The Parent Invention described how to determine a set of parameters such as the three parameters $\alpha_i(p_i, \lambda), \mu_i(p_i, \lambda), S_i(p_i, \lambda)$ that can characterize the colorimetric properties of this ink layer as it pertains to overprints of several such layers. Here, $p_i$ is the amount of ink in this (the $i^{th}$) ink layer, with the amount expressed as a fraction between 0 and 1, and $\lambda$ is the wavelength of the light radiation. Using such parameters, when there is no interaction between the layers, the reflectance spectrum $R_i(\lambda)$ of the $i^{th}$ ink layer can be determined by applying the following equation recursively $$R_i(\lambda) = (1 - \alpha_i(p_i, \lambda)) * R_{i-1}(p_i, \lambda)^{\mu_i(p_i, \lambda)} + S_i(p_i, \lambda), \quad (1)$$

with $R_0(\lambda)$ being the spectrum of the bare substrate.

When there is interaction possible between the ink layers, then these parameters each become a function also of the amounts of ink in the other layers. In general this includes both the layers under and the layers over this $i^{th}$ ink layer. In addition, the "optically perceived" ink coverage (denoted $p'_i$) is changed from the actual applied amount of ink $p_i$ by the interaction between the layers. Denoting the changed parameter and ink amount with a prime, the interaction of all the layers leads to the change $$p_i \to p'_i(\lambda, p_1, p_2, \ldots, p_n), \quad (2)$$

$$\alpha_i \to \alpha'_i(\lambda, p_1, p_2, \ldots, p_n), \quad (3a)$$

$$\mu_i \to \mu'_i(\lambda, p_1, p_2, \ldots, p_n), \quad (3b)$$

and $$S_i \to S'_i(\lambda, p_1, p_2, \ldots, p_n) \quad (3c)$$

Thus each quantity in general becomes a function of wavelength and all the coverage amounts. Consider first $p'_i$, the ink quantity for this layer as a function of the other ink quantities and $\lambda$. $p'_i$ can be written as $$p'_i = p_i + \Delta p_i + \Delta p'_i, \quad (4)$$

where $p'_i$ is the observed equivalent ink amount, $p_i$ is the actual laid ink amount, $\Delta p_i$ denotes the change due to the other inks deposited under and over this (the $i^{th}$ ink) and $\Delta p'_i$ is the change between the laid ink and the observed amount of ink when there are no other inks. $\Delta p'_i$, for example, may represent the dot gain.

There are two factors potentially contributing to the changes ($\Delta p_i$), the changes due to the inks under this (the $i_{th}$) ink layer (for example, trapping), and those due to inks above this layer (for example, spreading). That is, $$\Delta p_i = \Delta p_i|_{higher\ layers} + \Delta p_i|_{lower\ layers}. \quad (5)$$

The influence of the inks under this layer may be written, for example, as $$\Delta p_i|_{higher\ layers} = h_i(p_i, \lambda)\left(1 - \prod_{j=i+1}^{n}(1 - p'_j)\right), \text{ and} \quad (6a)$$

$$\Delta p_i|_{lower\ layers} = \tilde{h}_i(p_i, \lambda)\left(1 - \prod_{j=1}^{i-1}(1 - p'_j)\right). \quad (6b)$$

By neglecting the second order changes in the ink amounts in these expressions, the expressions can be re-written (in approximate form) as $$\Delta p_i|_{higher\ layers} = h_i(p_i, \lambda)\left(1 - \prod_{j=i+1}^{n}(1 - p''_j)\right), \text{ and} \quad (7a)$$

$$\Delta p_i|_{lower\ layers} = \tilde{h}_i(p_i, \lambda)\left(1 - \prod_{j=1}^{i-1}(1 - p''_j)\right). \quad (7b)$$

where $p''_j$ is the apparent ink amount when an ink amount $p_j$ is deposited with no other inks present. For example, may be the changed ink amount due to dot gain. Mathematically, $$p''_j = p_j + \Delta p'_j. \quad (8)$$

Combining, these equations gives $$p'_i = p''_i + h_i(p_i, \lambda)\left(1 - \prod_{j=i+1}^{n}(1 - p''_j)\right) + \tilde{h}_i(p_i, \lambda)\left(1 - \prod_{j=1}^{i-1}(1 - p''_j)\right), \quad (9a)$$

or alternatively, $$\Delta p_i = h_i(p_i, \lambda)\left(1 - \prod_{j=i+1}^{n}(1 - p''_j)\right) + \tilde{h}_i(p_i, \lambda)\left(1 - \prod_{j=1}^{i-1}(1 - p''_j)\right). \quad (9b)$$

Now each of the parameters $\alpha, \mu$ and S, which, when there is no interaction between ink layers, are functions of $p_i$, the amount of ink on this (the $i^{th}$) ink layer, and of the wavelength, now become functions also of the different amounts of inks laid under and over the layer of interest. This in general causes the "effective" parameters to change from the actual parameters. By "effective" parameters is meant that the reflectance may be determined from these "effective" parameters (denoted $\alpha'_i(p_i, \lambda)$, $\mu'_i(p_i, \lambda)$, and $S'_i(p_i, \lambda)$, respectively) using $$R_i(\lambda) = (1 - \alpha'_i(p_i, \lambda))^* R_{i-1}(p_i, \lambda)^{\mu'_i(p_i, \lambda)} + S'_i(p_i, \lambda) \quad (10)$$

recursively, where * indicates multiplication.

The new effective parameters may be written in terms of the change of the apparent amount of ink, $\Delta p_i$, in the form $$\alpha'_i = \alpha_i(p_i, \lambda) + \Delta \alpha_i(p_i, \lambda)\Delta p_i, \quad (11a)$$

$$\mu'_i = \mu_i(p_i, \lambda) + \Delta \mu_i(p_i, \lambda)\Delta p_i, \quad (11b)$$

and $$S'_i = S_i(p_i, \lambda) + \Delta S_i(p_i, \lambda)\Delta p_i, \quad (11c)$$

where the dependence of each of these parameters is on the wavelength and on the ink amounts $p1, p2, \ldots, p_n$. Eqs. (11a)–(11c) use the reasonable assumption that the ink parameters are a function of the ink layer thickness, and that the ink volume is approximately constant before and after any interaction between the ink layers.

It can be seen that in order to determine $p'_i$, the ink quantity for this layer as a function of the other ink quantities and $\lambda$, and $\alpha'_i$, $\mu'_i$, and $S'_i$, the three ink parameters as functions of the ink quantities and $\lambda$, one needs to determine the eight quantities $h_i(p_i, \lambda)$, $\tilde{h}_i(p_i, \lambda)$, $\alpha_i(p_i, \lambda)$, $\mu_i(p_i, \lambda)$, $S_i(p_i, \lambda)$, $\Delta \alpha_i(p_i, \lambda)$, $\Delta \mu_i(p_i, \lambda)$, and $\Delta S_i(p_i, \lambda)$.

The preferred embodiment for so determining these quantities is to print s series of step wedges, measure the reflectances, and then apply Eqs. (9), (10), and (11a)–(11c) to form a set of equations in the unknowns. These equations are then solved numerically.

In particular, one prints four step wedges on four unequal backgrounds: two lightly colored backgrounds, a medium dark background, and a dark background. In the preferred embodiment, the lightly colored background is the bare substrate, called white (w), and the other three backgrounds are obtained by pre-printing the bare background with a first grey background, being light grey (g1), a second darker grey background, called grey 2 (g2), and a black background (k). The two grey backgrounds and the black background can be obtained by printing on a white substrate with grey and black colorants, but in the preferred embodiment for the case of offset printing are obtained using halftone, by printing two different medium halftone screen and a dark halftone screen using black colorant. In particular, these three pre-printed backgrounds are obtained by printing a 25%, a 50% and a 100% halftone area using 100% black ink. Each of the wedges preferably are halftone areas using the colorant and include 11 steps from 0 to 100% in steps of 10 percentage points. That is, each $p_i$ (not as a percentage) varies from 0 to 1.0 in steps of 0.1. One then measures the 44 reflectance spectra, preferably with a spectrophotometer. Each patch print of a particular coverage percentage is considered to be a colorant layer. That is, one ignores the microscopic look (the halftone pattern, etc.) of each patch.

The printing of the gradation steps on the four backgrounds is shown in FIG. 1. Shown on white substrate 105 are eleven patches, denoted 103-0 through 103-100, with 0% through 100% coverage, respectively. Also shown on the first greyish substrate 107 are eleven patches, denoted 109-0 through 109-100, with 0% through 100% coverage, respectively. Also shown on the second greyish substrate 111 are eleven patches, denoted 113-0 through 113-100, with 0% through 100% coverage, respectively. Finally, also shown on blackish substrate 115 are eleven patches, denoted 115-0 through 115-100, with 0% through 100% coverage, respectively.

Let these measurements be denoted as follows:

$R(w, p, \lambda)$: the reflectance spectrum of p patch on white;

$R(g1, p, \lambda)$: the reflectance spectrum of p patch on grey 1;

$R(g2, p, \lambda)$: the reflectance spectrum of p patch on grey 2;

$R(k, p, \lambda)$: the reflectance spectrum of p patch on black;

$R_w(\lambda)$: the reflectance spectrum of white=$R(\lambda)$=$R_{bg}(\lambda)$, the reflectance spectrum of the bare substrate;

$R_{g1}(\lambda)$: the reflectance spectrum of grey 1;

$R_{g2}(\lambda)$: the reflectance spectrum of grey 2; and $R_k(\lambda)$: the reflectance spectrum of black.

Let l indicate one of the backgrounds w, g1, g2, or k. Then from Eq. (10), $$R(l, p, \lambda)=(1-\alpha'(l, p, \lambda)))^*R_l(\lambda)^{\mu'(l, p, \lambda)}+S'(l, p, \lambda), \qquad (12)$$

and from Eqs. (9b) and (11a)–(11c), $$\alpha'(l, p, \lambda)=\alpha(p, \lambda)+\Delta\alpha(p, \lambda)\Delta p_l, \qquad (13a)$$

$$\mu'(l, p, \lambda)=\mu(p, \lambda)+\Delta\mu(p, \lambda)\Delta p_l, \qquad (13b)$$

$$S'(l, p, \lambda)=S(p, \lambda)+\Delta S(p, \lambda)\Delta p_l, \qquad (13c)$$

and $$\Delta p_l=p'-p''=\hbar(p, \lambda)p''_l \qquad (14)$$

where in Eq. (14), p' is the changed (apparent) amount of ink in the patch, p" is the amount seen due only to such phenomena as dot gain, i.e., the amount measured on the base background, and p"$_l$ is the apparent amount of ink used to print the background (grey 1, grey 2, or black). With the white (bare) background, by definition, p'=p" and $\Delta p$=0.

One now prints an additional layer, preferably of a neutral ink, say a third grey called grey (g) over all the step wedges, either by using the initially printed step wedges shown in FIG. 1, or by printing a new set of wedges with the overprinting with the third grey. One now again measures the 44 reflectance spectra, preferably with a spectrophotometer.

Figure 2:
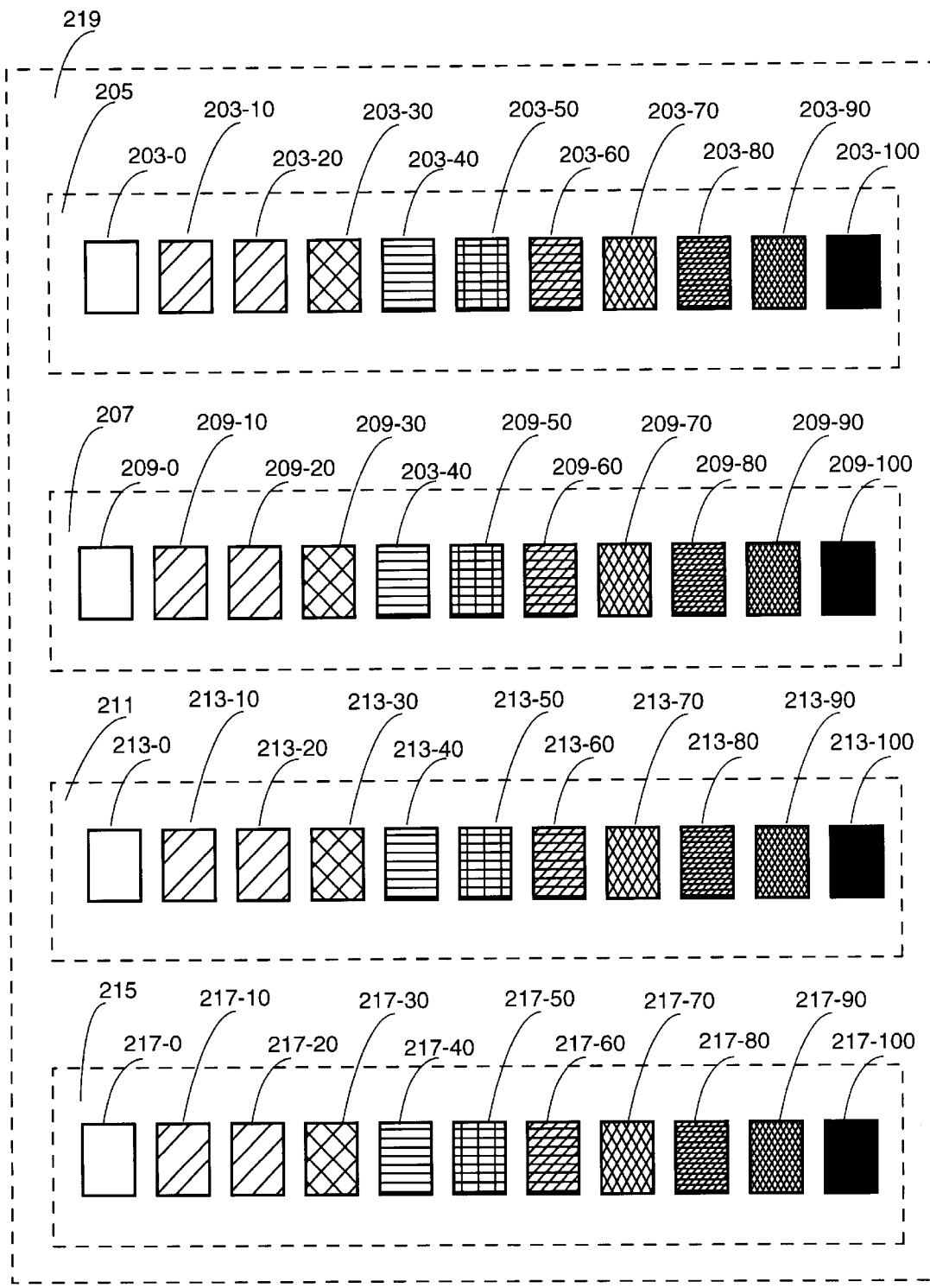
FIG. 2 shows the second set of prints made and measured in order to determine the colorant parameters for the case that includes scattering according to one embodiment of the method of the invention.

The printing of the gradation steps on the four backgrounds followed by the printing of a third grey is shown in FIG. 2. Shown on white substrate 205 are eleven patches, denoted 203-0 through 203-100, with 0% through 100% coverage, respectively. Also shown on the first greyish substrate 207 are eleven patches, denoted 209-0 through 209-100, with 0% through 100% coverage, respectively. Also shown on the second greyish substrate 211 are eleven patches, denoted 213-0 through 213-100, with 0% through 100% coverage, respectively. Finally, also shown on blackish substrate 215 are eleven patches, denoted 215-0 through 215-100, with 0% through 100% coverage, respectively. Finally, a third area is shown printed with a third grey colorant 219. The three grey backgrounds and the black background are again obtained by printing on a white substrate using halftone, by printing two different medium halftone screen and a dark halftone screen using black colorant, and then overprinting with a third grey halftone screen. As before, grey colorants may alternatively be used.

Suppose the parameters of the last grey overprint are not effected by the previously laid layers. In such a case, the measurements may be written as $$R''(l, p, \lambda)=(1-\alpha_g(\lambda)))^*R'(l, p, \lambda)^{\mu_g(\lambda)}+S_g(\lambda), \qquad (15)$$

where $R'(l, p, \lambda)$ are the spectra under this third grey layer as calculated using the modified parameters $\alpha''(l, p, \lambda)$, $\mu''(l, p, \lambda)$, and $S''(l, p, \lambda)$, l is one of w, g1, g2, or k, and parameters $\alpha_g(\lambda)$, $\mu_g(\lambda)$, and $S_g(\lambda)$ are the three parameters for the grey color overprint, which for example may be determined from the p=0 patches (using either g1 or g2) according to the method described in the Parent Invention. Hence, $$R'(l, p, \lambda)=(1-\alpha''(l, p, \lambda)))^*R_l(\lambda)^{\mu''(l, p, \lambda)}+S''(l, p, \lambda). \qquad (16)$$

In addition, $\alpha''(l, p, \lambda)$, $\mu''(l, p, \lambda)$, and $S''(l, p, \lambda)$ are now affected both by the background and the third grey overprint. Hence, $$\alpha''(l, p, \lambda)=\alpha(p, \lambda)+\Delta\alpha(p, \lambda)\Delta p_l, \qquad (17a)$$

$$\mu'(l, p, \lambda)=\mu(p, \lambda)+\Delta\mu(p, \lambda)\Delta p_l, \qquad (18b)$$

$$S'(l, p, \lambda)=S(p, \lambda)+\Delta S(p, \lambda)\Delta p_l, \qquad (19c)$$

and $$\Delta p_l=p'-p''=\hbar(p, \lambda)p''_l+h_i(p_i, \lambda)p''_g \qquad (20)$$

where in Eq. (20), p' is the changed (apparent) amount of ink in the patch, p" is the amount seen due only to such phenomena as dot gain, i.e., the amount measured on the base background, p"$_l$ is the apparent amount of ink used to print the background (grey 1, grey 2, or black), and p"$_g$ is the apparent amount of the third grey ink (grey) used for the final overprint. With the white (bare) background, by definition, p'=p".

One substitutes Eqs. (14) and (20) into each of Eqs. (13a)–(13c) and (19a)–(19c) to obtain the following six equations:

$$\alpha'(l, p, \lambda)=\alpha(p, \lambda)+\Delta\alpha(p, \lambda)\hbar(p, \lambda)p''_l, \qquad (21a)$$

$$\mu'(l, p, \lambda)=\mu(p, \lambda)+\Delta\mu(p, \lambda)\hbar(p, \lambda)p''_l, \qquad (21b)$$

$$S'(l, p, \lambda)=S(p, \lambda)+\Delta S(p, \lambda)\hbar(p, \lambda)p''_l, \qquad (21c)$$

$$\alpha''(l, p, \lambda)=\alpha(p, \lambda)+\Delta\alpha(p, \lambda)(\hbar(p, \lambda)p''_l+h_i(p_i, \lambda)p''_g), \qquad (22a)$$

$$\mu'(l, p, \lambda)=\mu(p, \lambda)+\Delta\mu(p, \lambda)(\hbar(p, \lambda)p''_l+h_i(p_i, \lambda)p''_g), \qquad (22b)$$

and $$S'(l, p, \lambda)=S(p, \lambda)+\Delta S(p, \lambda)(\hbar(p, \lambda)p''_l+h_i(p_i, \lambda)p''_g). \qquad (22c)$$

Eqs. (15) (21a)–(21c), (16), and (22a)–(22c) form 8 equations in the eight unknowns $h(p, \lambda)$, $\hbar(p, \lambda)$, $\alpha(p, \lambda)$, $\mu(p,$ $\lambda$), S(p, $\lambda$), $\Delta\alpha$(p, $\lambda$), $\Delta\mu$(p, $\lambda$), and $\Delta$S(p, $\lambda$). One now solves these equations numerically to determine these eight parameters for each of the ink amounts p for the particular ink. In the preferred embodiment, the technique of conjugate directions is used. In the preferred embodiment, the spectra are sampled in $\lambda$, and in particular, the following 36 wavelengths are used for these spectra: 380 nm, 390 nm, 400 nm, . . . , 720 nm, and 730 nm. The particular error function used for the conjugate directions minimization is the sum of squared deviations.

One also could print more inks on top of the four step wedges on the four different backgrounds and some form of minimization algorithm to form the eight unknowns, or alternatively, one could print fewer backgrounds with more inks over these backgrounds to determine the required number of measurements to be able to determine the four unknowns. The general principle is to make a number of prints over a number of different backgrounds and overprinted areas to form a sufficient number of measurements to solve for the four unknowns.

Note that for values of p other than those printed, in one embodiment, one determines the reflection spectra for the prints interpolating between the reflection spectra of the colorant coverage percentages that were measured, then applies the above equations to determine the colorant parameters. In another embodiment, one determines the spectral parameters of the colorant for any non-measured required coverage percentage p by interpolating between the spectral parameters of the colorant for the coverage percentages which were measured.

The following is the preferred procedure for determining an overprint of n inks, each denoted by subscript i, the overprint including amount $p_i$ of ink i, with the parameters $h_i(p_i, \lambda)$, $\tilde{h}_i(p_i, \lambda)$, $\alpha_i(p_i, \lambda)$, $\mu_i(p_i, \lambda)$, $S_i(p_i, \lambda)$, $\Delta\alpha_i(p_i, \lambda)$, $\Delta\mu_i(p_i, \lambda)$, and $\Delta S_i(p_i, \lambda)$ for each of the n inks known, for example from the determining method described above.

1. Determine the quantities $p''_j$ by laying down quantities $p_j$ and making measurements, or from other dot gain information about the colorant with the particular press on the particular substrate.
2. Using these measurements, determine the quantities $$\left(1 - \prod_{j=1}^{i-1}(1 - p'_j)\right) \approx \left(1 - \prod_{j=1}^{i-1}(1 - p''_j)\right), \text{ and}$$

$$\left(1 - \prod_{j=i+1}^{n}(1 - p'_j)\right) \approx \left(1 - \prod_{j=i+1}^{n}(1 - p''_j)\right) \text{ for}$$

each of the inks.

3. Determine $\Delta p_i$ according to $$\Delta p_i = h_i(p_i, \lambda)\left(1 - \prod_{j=i+1}^{n}(1 - p''_j)\right) + \tilde{h}_i(p_i, \lambda)\left(1 - \prod_{j=1}^{i-1}(1 - p''_j)\right). \tag{9b}$$

4. Determine the modified parameters that include the effect of other layers according to $$\alpha'_i = \alpha_i(p_i, \lambda) + \Delta\alpha_i(p_i, \lambda)\Delta p_i, \tag{11a}$$

$$\mu'_i = \mu_i(p_i, \lambda) + \Delta\mu_i(p_i, \lambda)\Delta p_i, \tag{11b}$$

and $$S'_i = S_i(p_i, \lambda) + \Delta S_i(p_i, \lambda)\Delta p_i. \tag{11c}$$

5. Use the modified parameters to recursively determine the overprint using $$R_i(\lambda) = (1 - \alpha'_i(p_i, \lambda))^* R_{i-1}(p_i, \lambda)^{\mu'_i(p_i, \lambda)} + S'_i(p_i, \lambda) \tag{10}$$

with initially $R_0(p_i, \lambda) = R_{bg}(\lambda)$, the reflectance spectrum the bare substrate.

To predict the color resulting from printing multiple inks consecutively with a certain ink coverage (e.g., dot percentage) on top of each other, therefore, in the case of there being no interaction between the different ink layers, the invariance property of the colorant parameters is used. One can regard a substrate with a colorant printed on it as a substrate of the same type, but having a different color, and one can now determine the color spectrum of laying a second colorant over this first colorant. Thus, according to one embodiment of the method of this invention, to predict the color resulting from printing multiple inks consecutively with a certain ink coverage (e.g., dot percentage) on top of each other, the method applies Eq. (1) repeatedly in the particular printing order. That is, one then applies Eq. (1) to determine an overprint formed by laying down different colorants in a particular order. One starts with $R_0(\lambda) = R_{bg}(\lambda)$ representing the reflectance of the raw substrate, and uses Eq. (1) to determine as $R_p(\lambda)$, $R_{p1}(\lambda)$ of $p_1\%$ of the first colorant applied. One now repeats the calculation by substituting for $R_{bg}(\lambda)$ in Eq. (1) the $R_{p1}(\lambda)$ obtained by laying down the first colorant on the substrate, and calculating a new $R_p(\lambda)$, $R_{p2}(\lambda)$ representing the result of laying down $p_2\%$ of a second colorant. This can be repeated for a number of colorants in different amounts deposited on a substrate in different order.

In the case of there being interaction between the layers possible, five additional parameters, $h_i(p_i, \lambda)$, $\tilde{h}_i(p_i, \lambda)$, $\Delta\alpha_i(p_i, \lambda)$, $\Delta\mu_i(p_i, \lambda)$, and $\Delta S_i(p_i, \lambda)$, and determined in addition to the three parameters $\alpha_i(p_i, \lambda)$, $\mu_i(p_i, \lambda)$, and $S_i(p_i, \lambda)$ for each of the n inks. The procedure described in steps (1)–(4) above are then followed to determine the three "effective" parameter values $\alpha'_i, \mu'_i$, and $S'_i$. One now applies Eq. (10) exactly the same as Eq. (1) for the non-interaction case.

The Derived Colorant Case

Figure 3:
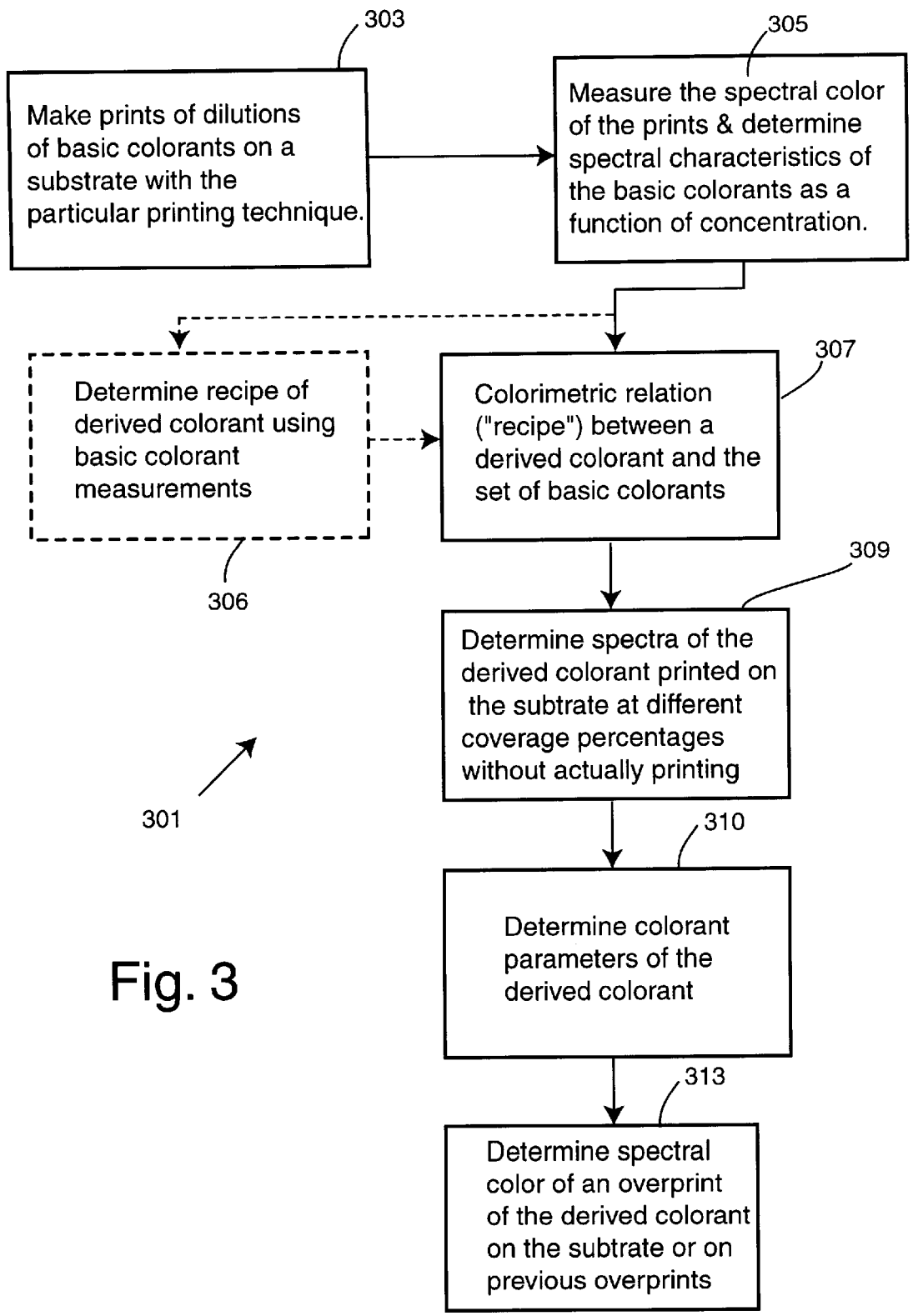
FIG. 3 shows a flowchart of the general steps of calculating the spectral color resulting from superimposing a colorant layer on a colored carrier, according to one embodiment of the method of the invention.

A modification of the method provides for characterizing any of a large set of colorants, called "derived colorants," whose color characteristics can be matched by mixing a small set of colorants, called "basic colorants," according to a recipe. The overall method is illustrated in FIG. 3. In step 303, a set of patches is made with varying amounts of each of the set of basic colorants on the particular substrate type of interest for a set of dilutions of the colorant. In step 305, measurements are made on the set of patches, and, treating each dilution and each coverage percentage as if it was a different colorant, spectral characterizations of each printed coverage percentage of each of the basic colorants is determined as a function of dilution. Using these characterizations of the basic colorants and knowledge of the recipe, shown as box 307, of how any derived colorant which is not a basic colorant is matched or made with basic colorants, one then determines in step 309 the spectra of a set of patches of varying halftone coverage percentages of the derived colorant on the particular substrate type of interest as if the set of patches printed in step 303 was printed with the derived colorant, and using these spectra, one also determines in step 310 the colorant parameters of the derived colorant. In step 313 one uses these colorant parameters to determine the reflection (or transmission) spectra for certain amounts of the derived colorant for a particular printing technique on a particular substrate type of a known color spectrum, shown as 311, without needing to make measurements or prints (or transparencies) using the derived colorant. If the recipe for the derived colorant is not known, then the method includes step 306 (shown dotted) of using knowledge of the desired color and determining the recipe from such knowledge and some of the measurements of the basic colorants of step 305. Thus, using steps 303, 305, 306 (when needed), 307, 309 and 310, one can characterize a very large number of possible colorants by making measurements on only a smaller set of basic colorants.

Details of the method applied to derived colorants are in the description of the Parent Invention, and how to modify the method to accommodate the larger number of colorant parameters needed when interaction between layers is possible would be clear to one in the art. Briefly, The preferred embodiment of the method of this invention applied to derived colorants starts by selecting a set of basic colorants. These basic colorants are selected so that they span the gamut of all the colorants (ie., the derived colorants) for which characterizations are desired for the particular printing technique on the particular substrate type. One now determines the colorant parameters of the basic colorants. In the simple case that the derived colorant has a one-to-one relationship with one of the selected basic colorants, the colorant parameters for the derived colorant are the colorant parameters of the basic colorant. The more complex case is when there is not a one-to- one relationship between the derived colorant and any one of the basic colorants. In such a case, the derived colorant is made of the basic colorants or has the same color characteristics as a colorant obtained from the basic colorants by using a recipe, that is, by mixing the basic colorants at a certain concentration, denoted $c_i$, with i=1, . . . , $n_c$, for the case of $n_C$ basic colorants. Using the well known one-constant Kubelka-Munk theory (see, for example, D. B. Judd and G. Wyszecki, *Color in Business, Science, and Industry*, New York: Wiley-Interscience, pp. 420–426, 1975), one can express the Kubelka-Munk constant and the color spectrum of a print with colorant coverage p % of a particular derived colorant using the following two relationships:

$$\left(\frac{K}{S}\right)_p (\lambda) = \quad (23)$$

$$\left(\frac{K}{S}\right)_{1p}(\lambda, c_1) + \left(\frac{K}{S}\right)_{2p}(\lambda, c_2) + \ldots + \left(\frac{K}{S}\right)_{np}(\lambda, c_n) + \left(\frac{K}{S}\right)_{substrate}(\lambda)$$

$$\left(\frac{K}{S}\right)_{substrate} = \frac{(1 - R_{substrate}(\lambda))^2}{2R_{substrate}(\lambda)}, \quad (24)$$

and $$\left(\frac{K}{S}\right)_{ip}(\lambda) = \frac{(1 - R_{ip}(\lambda))^2}{2R_{ip}(\lambda)} - \left(\frac{K}{S}\right)_{substrate}(\lambda), \quad (25)$$

where $R_{ip}(\lambda)$ is the reflection spectrum of basic colorant i with coverage percentage p and $R_{substrate}(\lambda)$ is the spectrum of the substrate. The inverse of Eq. (25) is $$R_{ip}(\lambda) = 1 + \left(\frac{K}{S}\right)_{ip}(\lambda) + \left(\frac{K}{S}\right)_{substrate}(\lambda) - \quad (26)$$

$$\sqrt{\left(\frac{K}{S}\right)_{ip}(\lambda) + \left(\frac{K}{S}\right)_{substrate}(\lambda) * \left[\left(\frac{K}{S}\right)_{ip}(\lambda) + \left(\frac{K}{S}\right)_{substrate}(\lambda) + 2\right]}.$$

Each of the $(K/S)_{ip}(\lambda)$ values are usually concentration ($c_i$) dependent and coverage percentage p dependent, as indicated by the notation $(KS)_{ip}(\lambda, c_i)$. In one embodiment of the method of the present invention, one makes a set of dilutions of each basic colorant with a dilutant suitable for the set of basic colorants. In the preferred embodiment of using the twelve basic CROMALIN® colors (E.I. du Pont de Nemours and Company, Wilmington, Del.) for the basic colorants, one makes six dilutions of each basic colorant with the CROMALIN® brand color "transparent white." The six dilutions are of 100%, 50%, 25%, 12%, 6% and 3%, respectively, of each basic colorant. Each such dilution is a colorant that can be characterized using the first part of the techniques described above for the single colorant description. In the preferred embodiment described herein with three-parameter characterization, this means that one makes (e.g., one prints in the preferred embodiment) gradation steps of each dilution of each basic colorant on four different backgrounds, a lightly colored, light-medium colored, and dark-medium colored and darkly colored substrate of the same type (called white, light-grey, dark-grey, and black, respectively). See FIGS. 1 and 2. For each dilution of each basic colorant, one prints four rasters (i.e., sets) of patches of that dilution of that colorant, one on white, one on grey and one on black. Each set of patches goes from 0% to 100% ink coverage (dot percentage in the preferred embodiment applicable to offset printing) in steps of 10% increments. In the preferred embodiment, there are 44 patches of 6 dilutions of 12 basic inks.

One now measures the spectrum of each patch. Using Eq. (7), one now determines the K/S value for each of the patches. Thus, for each basic colorant, one has the K/S value at six concentrations (the dilution values) at the 11 coverage percentages printed (including 0%). A derived colorant of interest is specified by its recipe $(c_1, \ldots, c_n)$ for the selected basic colorants. Based on this, one now interpolates in concentration to obtain for each of the printed colorant coverage percentages the values of K/S of each of the basic colorants at the appropriate concentration for that basic colorant, $c_i$ for the $i^{th}$ basic colorant, i=1, . . . , n. Linear interpolation is used in the preferred embodiment. By using Eq. (24) on measured $R_w(\lambda)$, $R_g(\lambda)$, and $R_k(\lambda)$, one also has the K/S values of the background substrates, so one now applies Eq. (23) to obtain the K/S value for the derived colorant for each of the coverage percentages that were printed with basic colorants on each of the three substrates. Using the inverse of Eq. (25), one now determines the spectra that would result if the derived colorant would have been printed with a number of gradation steps on three different backgrounds.

Thus by using the recipe (set of $c_i$), one has the calculated reflection spectra for the derived colorant printed on the four background substrates at the set of coverage percentages p at which the dilutions of the basic colorants were printed. From these eight calculated spectra, one determines the eight colorant parameters of the derived color in exactly the same way as done in the single colorant case. For coverage percentages (e.g., dot percentages) not printed, and thus for which no spectra are available, in one embodiment, one determines the reflection spectra for the prints on white, on grey and on black by interpolating between the reflection spectra of the coverage percentages that are available. Out of these calculated reflection spectra one can then calculate the colorant parameters as described above for a single colorant. In another embodiment, one determines the spectral parameters of the derived colorant for any non-measured required coverage percentage by interpolating between the spectral parameters of the derived colorant for the coverage percentages which were measured.

In an alternate embodiment, rather than the one-parameter Kubelka-Munk theory being used, the two-parameter is used. How to modify the step of determining the spectra of overprints of the derived ink from the recipe and from measurements of prints of dilutions of the basic colorants would be clear to one of ordinary skill in the art. In yet other alternate embodiments, other theories for mixtures of colorants may be used for this step.

If the recipe, i.e., the set of concentrations $c_i$, i=1, ..., n, of n basic colorants for any derived colorant for a printing technique on substrates of a particular type is unknown, it is necessary to determine it. Techniques for recipe determination are known in the art.

Thus, according to one embodiment of the method of the present invention, by characterizing a small number of basic colorants on one sample of a substrate of a particular type using a particular printing mechanism, one can predict the color appearance of an overprint of several colorants of a large set of colorants on any substrate of any color, the substrate being of the same particular type.

An apparatus for Determining Colorant Overprints

Another aspect of the present invention is an apparatus for determining the to spectrum of colorant overprints. As before this is applicable to both transmittance and reflection imaging, and only the reflection case will be described. How to extend to the case of transmission imaging would be clear to those of ordinary skill in the art.

Figure 4:
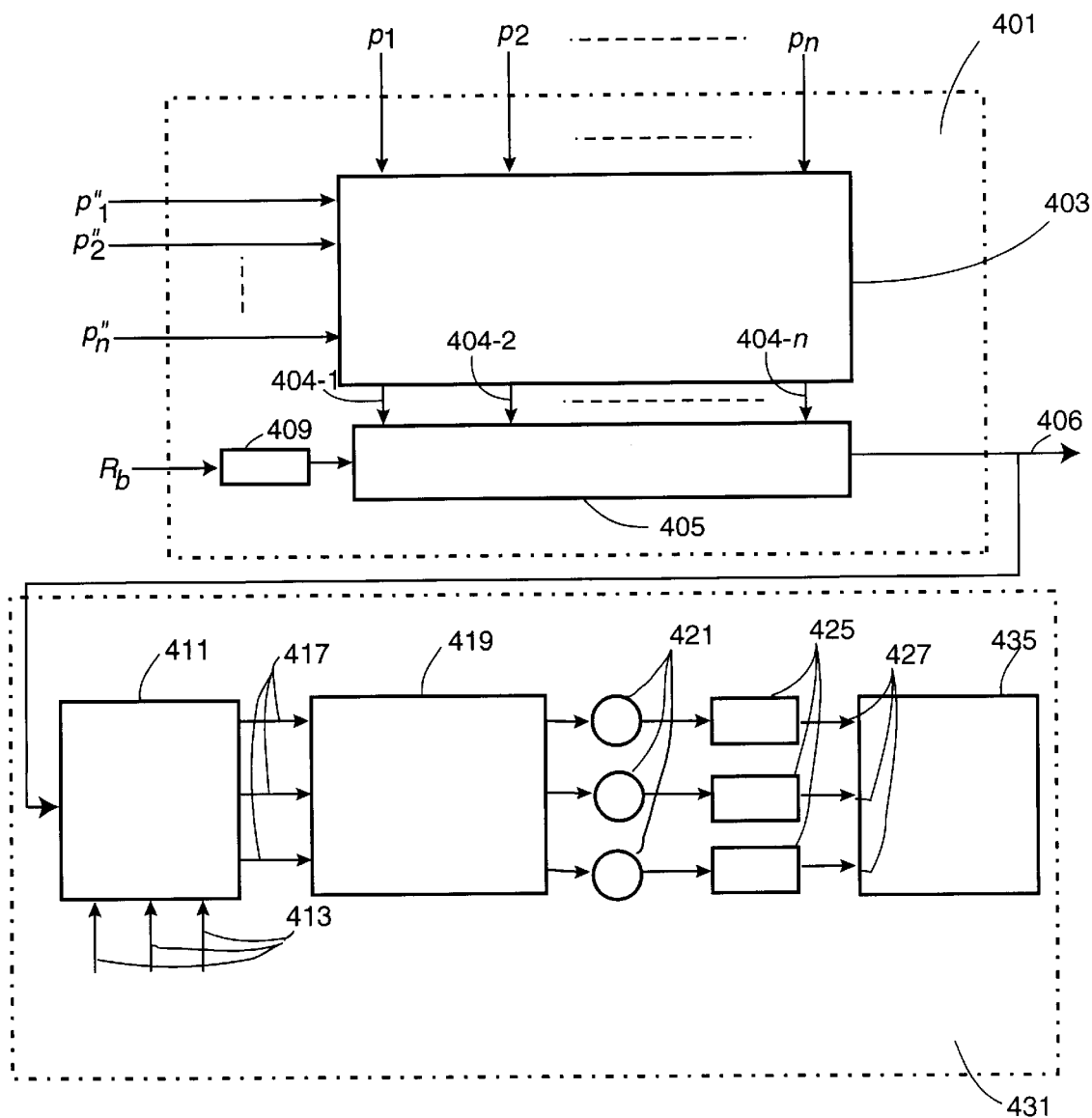
FIG. 4 shows an apparatus for determining the spectral color parameters of colorants and for determining the color spectrum of overprints according to an embodiment of the invention. Included in this diagram is an apparatus for using the color spectrum of overprints to simulate color appearance on a CRT display.

The preferred embodiment of the apparatus of the present invention is shown as item 401 in FIG. 4. An example will be followed of how apparatus 401 calculates the color spectrum of an overprint of n colorants with respective coverage percentages $p_1, \ldots, p_n$ on a background with background reflectance $R_0(\lambda)$. It is assumed that each of the colorants has been characterized, for example using one of the embodiments of CM the method of the present invention described above. That is, each colorant has been characterized by either two spectral parameters (no layer interaction, no scattering), three spectral parameters (no layer interaction, scattering), or more than three spectral parameters (layer interaction),. That is, each colorant has a set of $n_p$ colorant parameters.

Apparatus 401 has as input the reflection spectrum of the background $R_0(\lambda)$ and n signals representing the n colorant coverage amounts (dot percentages of inks for the case of offset printing) denoted $p_1, \ldots, p_n$, respectively. In the preferred embodiment, the spectrum is quantized into a finite number, $n_l$=36, of wavelengths $\lambda_1, \lambda_2, \ldots, \lambda_n$, so that $R_0(\lambda)$ consists of the 36 samples of the spectrum at the 36 wavelengths. Coupled to the spectrum input is a first memory 409 for storing the $n_l$ samples of the background spectrum $R_0(\lambda)$ at the $n_l$ wavelengths. Also included is a logic unit 403 coupled to the n inputs which determines, as n sets of outputs, denoted 404-1, 404-2, . . . , 404-n, respectively, the values of the modified colorant parameters (the functions $\alpha'(p, \lambda)$, $\mu'(p, \lambda)$ and $S'(p, \lambda)$, in the two-parameter case) for the n input p values $p_1, \ldots, p_n$, respectively, for all $n_l$ values of $\lambda$. Note that also input to unit 403 are the n values $p''_1, \ldots, p''_n$, respectively, which can also be derived from coverage percentage $p_1, \ldots, p_n$. These n outputs 404-1, 404-2, . . . , 404-n are coupled to a combiner unit 405 as inputs to 405. Combiner unit 405 also has a second input which is coupled to first memory 409 containing the background spectrum input $R_0(\lambda)$. The output 406 of combiner unit 405 is the color spectrum at the $n_l$ wavelengths resulting from overprinting the n colorants at coverage percentage $p_1, \ldots, p_n$, respectively, when deposited over the substrate. Combiner unit 405 sequentially uses for instance Eq. (10) for the case of scattering parameter-characterized colorants with interaction, or Eq. (1) for the three-parameter case with no interaction.

One implementation of logic unit 403 is a direct table lookup mechanism which includes a second memory, in particular RAM, for storage of the table. This mechanism is used for all possible input values of $p_1, \ldots, p_n$, and $p''_1, \ldots, p''_n$, for all wavelengths $n_l$ and for all colorant parameters. For the case of 8-bit quantities for $p_1, \ldots, p_n$ and $p''_1, \ldots, p''_n$, a reasonable amount of memory (e.g., RAM) is required to store the colorant parameters.

An alternate embodiment of logic unit 403 as n interpolation units is described in the Parent Invention, and such an alternate embodiment may readily be modified in include the additional inputs $p''_1, \ldots, p''_n$.

Figure 5:
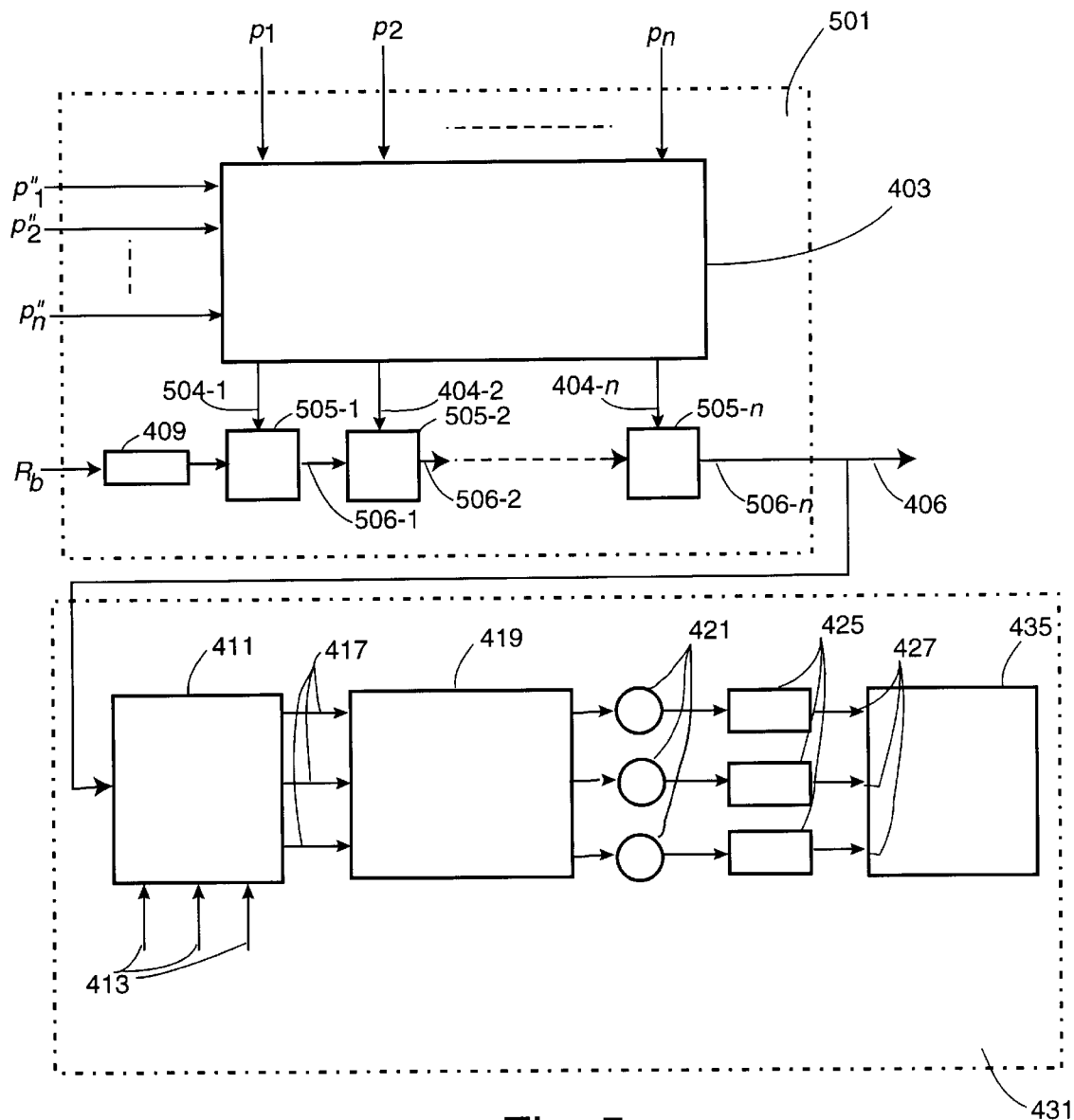
FIG. 5 shows one particular embodiment of the apparatus of FIG. 4 for determining the color spectrum of overprints. Included in this diagram is the apparatus from FIG. 4 for using the color spectrum of overprints to simulate color appearance on a CRT display.

The particular embodiment of combiner unit 405 shown in FIG. 5 is now described. The outputs 404-1, 404-2, . . . , 404-n of logic unit 603, are n sets of $n_p$ modified spectral colorant parameters at $p=p_1, \ldots, p_n$, respectively. These outputs are coupled to n arithmetic units 505-1, 505-2, . . . , 505-n, each arithmetic unit also having a second input. The second input of the first arithmetic unit 505-1 is coupled to first memory 409 containing the background spectrum input $R_0(\lambda)$. The second input of each subsequent arithmetic unit is coupled to the output of the previous arithmetic unit. The output of each arithmetic unit 505-i, i=1, . . . , n, is the color spectrum of the colorant of coverage percentage $p_i$ when deposited over the substrate only (for i=1) or when deposited over the substrate with all the colorants 1, . . . , i–1 deposited in order, for other values if i. Each arithmetic unit 505-i, i=1, . . . , n, uses for instance Eq. (10) for the case of three-parameter-characterized colorants with inter-colorant interactions. In one embodiment, each arithmetic unit 505-i, i=1, . . . , n, includes: (a) an exponentiation unit which, for each wavelength, exponentiates the value of the signal of the second input by the first colorant parameter from the first input, that is, determines (the second input)(the first colorant parameter of the first input), where  is exponentiation; (b) a multiplication unit which multiplies the result of the exponentiation by the value of the second colorant parameter from the first input; and c) an adder unit which adds for each wavelength the value of the third colorant parameter (if any) from the first input to the result of the multiplication and exponentiation. Thus, arithmetic unit 505-1 calculates the reflectance spectrum of the print of colorant 1 at coverage percentage $p_1$ on the substrate with spectrum $R_0$ resulting in a spectral color $R_{0+Color\ 1}(\lambda)$ In arithmetic unit 505-2, the effect of colorant 2 at coverage percentage $p_2$ is added by using the same method as arithmetic unit 505-1, but now $R_{0+Color\ 1}(\lambda)$ takes the place of the background color. The final output 506-n is the reflection spectrum 406 of the superimposition of all the colorant layers.

Figure 6:
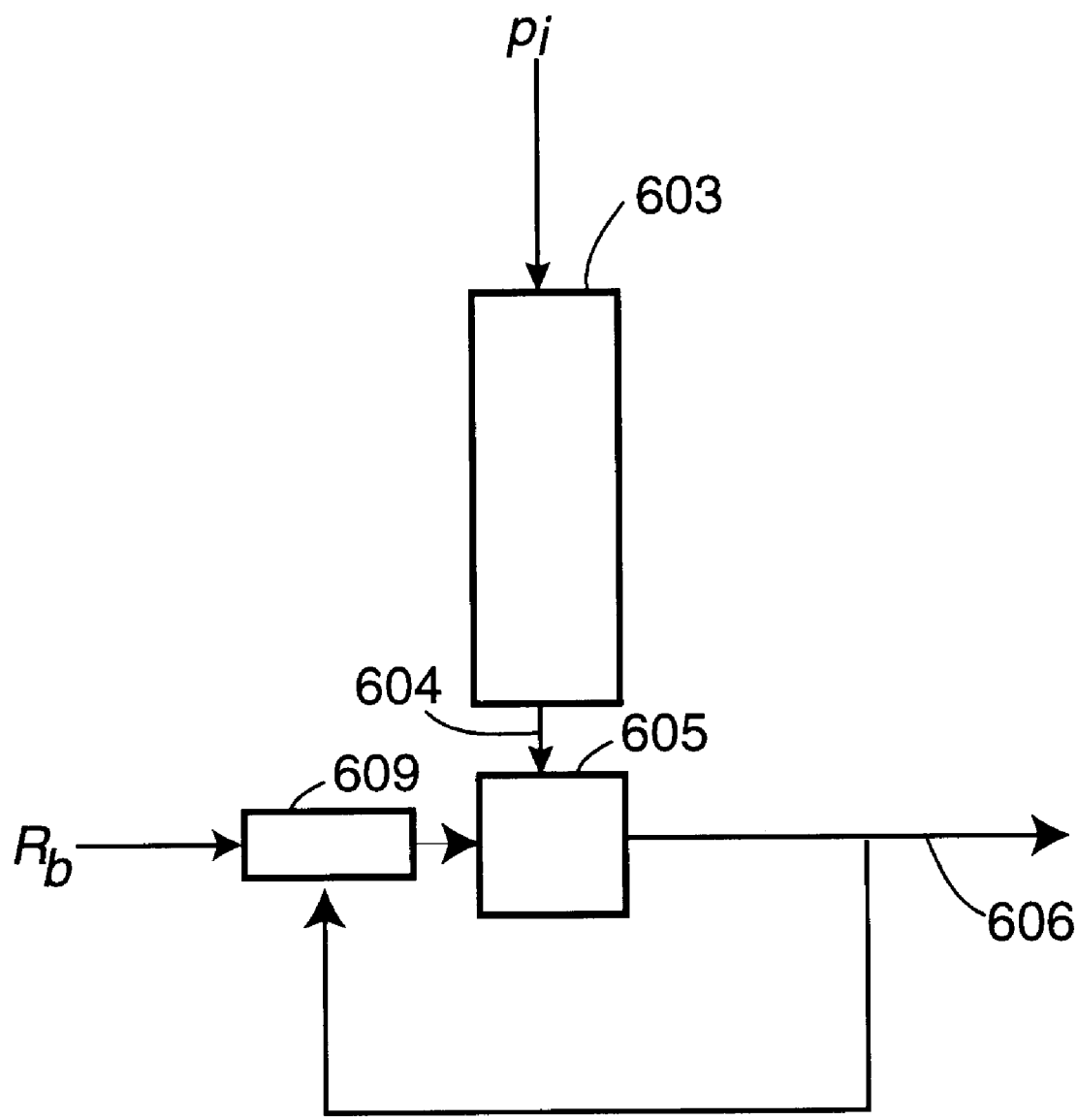
FIG. 6 shows an alternate implementation of the apparatus of FIG. 4 for determining the color spectrum of overprints according to an embodiment of the invention.

The above embodiment can be thought of as a "parallel" implementation of determining the overprints. In another embodiment, applicable to the case of no interaction between the colorant layers, logic unit 403, and the n arithmetic units implementing combiner unit 405 can be replaced by a single interpolation unit and a single arithmetic unit that operate in a serial manner in n cycles. This is shown in FIG. 6. Interpolation unit 603 has as an input the percentage of a colorant, and accepts as constants the values of the $n_p$ parameters for that colorant at a small number of coverage percentages at $n_l$ wavelengths. The output 604 of the interpolation unit 603 is the set of the values of the $n_p$ parameters for that colorant at the n, wavelengths for coverage percentage $p_l$. Output 604 is coupled to the first input of arithmetic unit 605. A second input of arithmetic unit 605 is coupled to the output of a storage buffer (a memory) 609 which stores a background spectrum. The output 606 of arithmetic unit 605 is the color spectrum at the $n_l$ wavelengths of the colorant deposited over a substrate with the spectrum of the second input of arithmetic unit 605. At initialization, storage buffer 609 accepts as input some spectrum $R_0(\lambda)$. At the end of each cycle, storage buffer 609 accepts as input the output spectrum of arithmetic unit 605 from the previous cycle. The serial device operates as follows. In the first cycle, interpolation unit 803 is loaded with the values of the $n_p$ parameters for the first colorant at $n_l$ wavelengths for the small set of coverage percentages, and the input of interpolation unit 603 is coupled with the number $p_1$. The output 604 of the interpolation unit 603 is then the value of the parameters of the first colorant at coverage percentage $p_1$. This is coupled to the first input of arithmetic unit 605. Storage buffer 609 is first loaded with the value of the substrate spectrum $R_0(\lambda)$. Thus at the end of the first cycle, the output 606 of the arithmetic unit is the spectrum of the substrate with a single overprint of the first colorant at coverage $P_1$. This is coupled to storage buffer 609. In each subsequent cycle, for example, the $i^{th}$ cycle, i=2, ..., n, the set of interpolators is loaded with the values of the $n_p$ parameters at the small number of coverage percentages for the $i^{th}$ colorant at $n_l$ wavelengths, and has as input the coverage percentage $p_l$. Storage buffer 409 contains the output spectrum corresponding to overprints of the of the (i−1) previous colorants. Thus, at the end of n cycles, the output 606 of arithmetic unit 605 is the spectrum 406 of the n overprints.

Not shown in apparatus 401 of FIG. 4, 501 of FIG. 5, and the apparatus of FIG. 6 are the control units necessary to operate the various blocks. Including such control units would be clear to those of ordinary skill in the art. Each of the blocks in apparatus 401 of FIG. 4, 501 of FIG. 5, and the apparatus of FIG. 6 may be implemented in various ways. For example, each may be implemented as a set of computer instructions operating on a computer system. Alternatively, some or all blocks may be built using special hardware, for example using digital signal processor ("DSP") devices, or using programmable logic, or using special purpose logic, for example, one or more application specific integrated circuits ("ASICs"). It would be clear to those in the art that many ways of implementing the apparatus is possible, and how to design such specific implementations would be clear to those of ordinary skill in the art.

In practice, the method is used to predict the color of an image comprising of pixels, and thus, includes predicting many overprints, each corresponding to a pixel in the image.

Method and Apparatus of Simulating Prints on a Proof Printer or on a Display

Another aspect of the invention is a method and apparatus for determining color values, for example CIE XYZ values or CIE-Lab or other color values of an overprint of n colorants on a substrate using the colorant parameters determined according to the above aspects of the invention. Yet another aspect is using these color values for simulating the visual appearance of an overprint of n colorants on a substrate on a display, for example, CRT monitor 435 of a display subsystem a computer system, or on a printer, for example, a proof printer. The emphasis of the description herein is on an apparatus for such determination, and it would be clear to those of ordinary skill in the art from this description how to implement the conversions and simulations as a method.

In practice, the color values are those of an image comprising of pixels, and thus, determining the color values of an overprint is repeated for many overprints, each corresponding to a pixel in the image.

Additional apparatus for these aspects of the invention is shown as apparatus 431 in FIG. 4. One may apply one or more of the embodiments of the method and apparatus of the present invention to determining color values, for example CIE XYZ values of an overprint of n colorants on a substrate. Similarly, CIE-Lab or other values may alternatively be determined. In another aspect of the present invention, these CIE-XYZ values can then be converted to RGB values to produce RGB signals to drive a color monitor, for example, CRT monitor 435. The image on the CRT is then used as an accurate simulation of the overprint of the n colorants. In FIG. 4, controller and CRT display 431 includes the hardware apparatus for displaying the overprint, and takes as input the reflection spectrum 406 which is the output of apparatus 401. As stated above, these blocks also may be implemented as a set of method steps implemented on a computer. The spectrum from apparatus 401 or another alternate apparatus is fed into a color values converter, shown as 411. In the preferred embodiment of the apparatus, $3^*n_l$ multiplier adders are used, which have as additional input the CIE illuminant-observer weightings 413. The output 417 is the set of CIE-XYZ values. How to carry out this conversion operation from a spectrum to CIE values is known in the art. The CIE-XYZ values 417 are fed into color coordinate converter, which preferably includes a 3×3 matrix multiplier 419, three adders 421, and three lookup tables 425 with the adder outputs as inputs, the lookup tables for gamma correction to produce the RGB signals 427 which are then fed into CRT monitor 435. How to carry out the transformation of the color coordinate converter from CIE-XYZ to RGB values is known in the art. The resulting image visualized on monitor 435 is a very accurate visualization of the overprint.

In another aspect of the present invention, the CIE-XYZ values 417, or the RGB values from lookup tables 425 may be fed to a multi-dimensional interpolator to determine the device dependent color values of a particular printing device such as a printer. The output of this interpolator can be sent to such a printing device. One practical application is color proofing, where the printing device is a proofing printer. The print resulting from such a printer is then an accurate simulation on the medium of the proofer of the overprint of the n colorants on the original substrate of spectrum $\underline{R}_0$. How to carry out color conversions from CIE-XYZ values or CIE-Lab values to the device color space of a particular printing device is known in the art.

In one preferred embodiment as a method for simulating the appearance of the overprint of the colorants on a printer, for example a proof printer, the simulation on a printer is a set of computer implemented method steps. These steps can be incorporated in a raster image processor ("RIP") system used to drive the printer.

As would be clear to those of ordinary skill in the art, each of the blocks in apparatus 631 and of the analogous method may be implemented in various ways, for example, as a set of computer instructions operating on a computer system or as special hardware which might use one or more DSPs or ASICs.

Experimental Results

Two sets of experiments were conducted to verify the model. In the first experiment, we considered a single colorant and printed it on substrates with various colors. These prints were measured and from the measurements we determined the colorant parameters for this colorant for each of the considered substrate colors. Then we compared the different colorant parameters, as they were determined from the prints on the different substrate colors. This verified that indeed the colorant obtained parameters are substantially independent of this substrate color.

Figure 7:
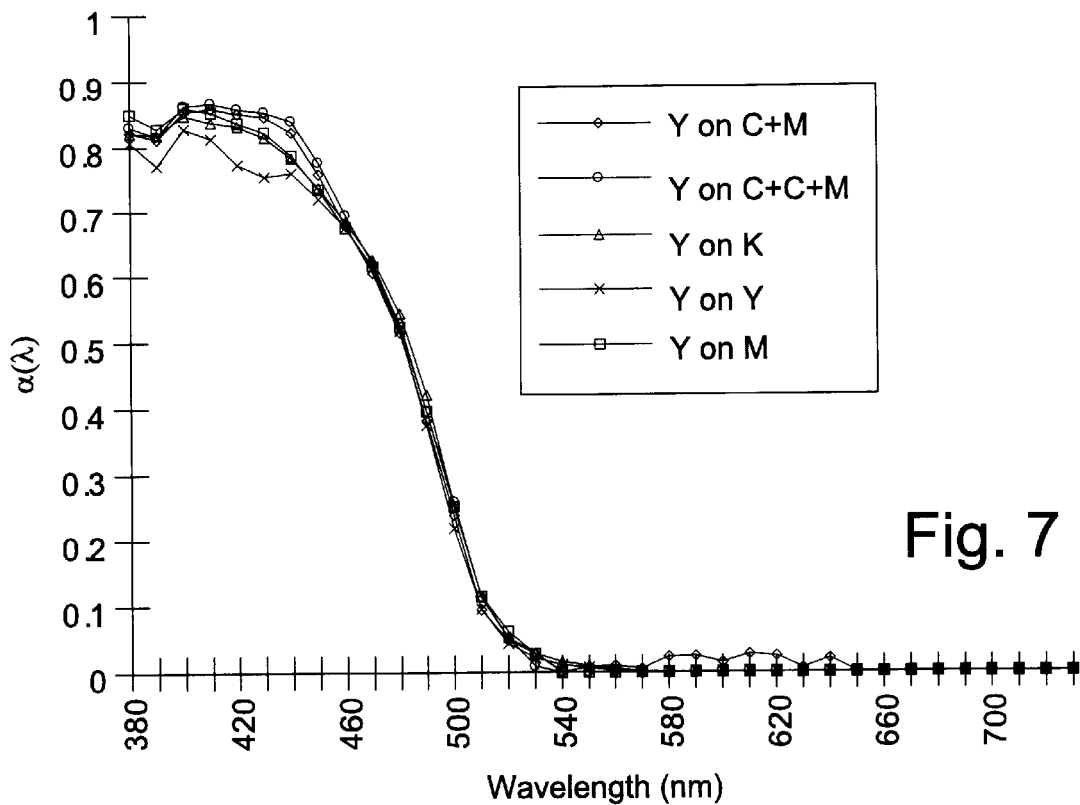
FIG. 7 shows experimental results of determining the colorant parameter $\alpha(\lambda)$ for 100% yellow on different substrate colors using the MATCHPRINT® process.
Figure 8:
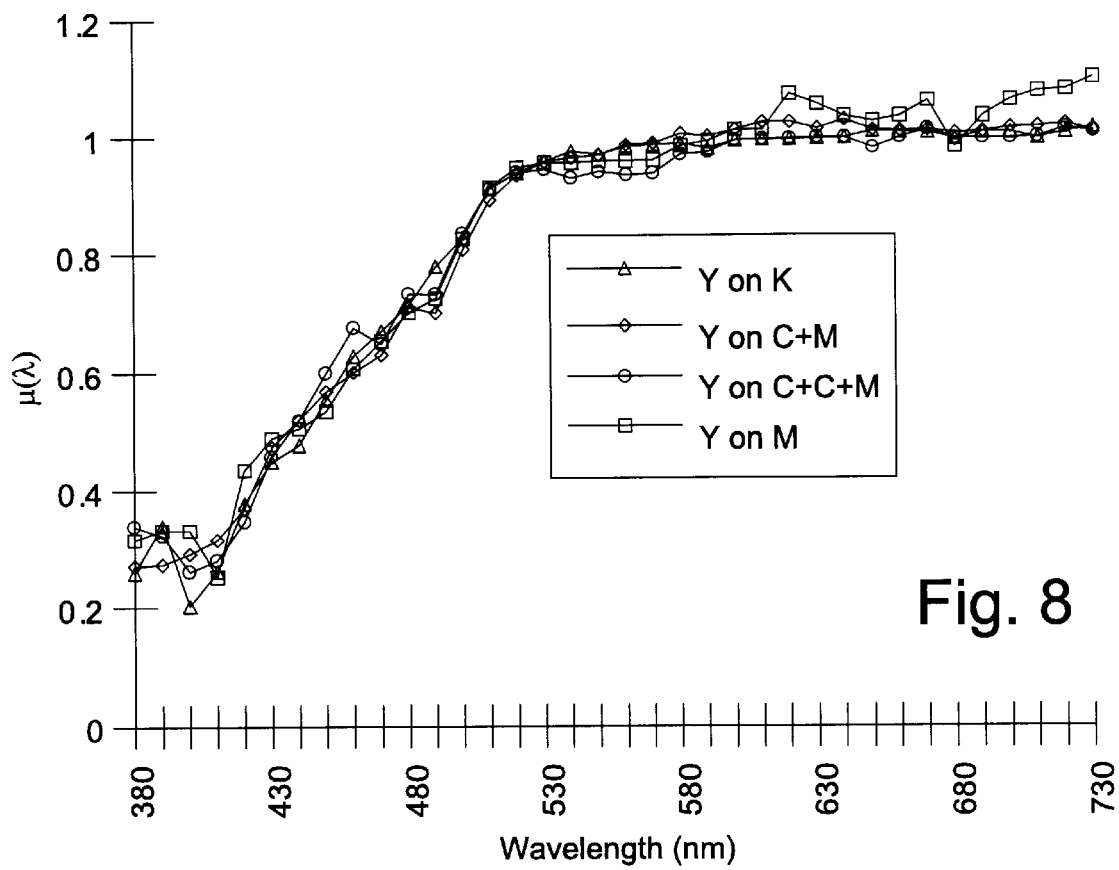
FIG. 8 shows experimental results of determining the colorant parameter $\mu(\lambda)$ for 100% yellow on different substrate colors using the MATCHPRINT® process.

FIG. 7 and FIG. 8 show the colorant parameters $\alpha(\lambda)$ and $\mu(\lambda)$ for a 100% Yellow on different substrate colors. This colorant had practically no scattering component S. The printing technique used in this experiment was MATCH-PRINT® (Imation, Inc., Oakdale, Minn.). The different substrate colors were obtained by first putting another colorant on the white substrate and in this case there was no interaction between the colorant layers observed.

In the case of no interaction between the colorant layers, the invariance of the colorant parameters with respect to the substrate color enables the parameters be used to predict the spectral reflectance when this colorant is put on an arbitrary substrate with an arbitrary color. The observed "roughness" in the curves of FIG. 7 and FIG. 8 come from the fact that the parameters were obtained only for a discrete number of wavelengths, and this roughness can be reduced by applying a fitting technique to the curves.

It should also be noted that yellow is a difficult colorants for which to determine the colorant parameters, since the absorption and interaction parameter $\alpha(\lambda)$ and $\mu(\lambda)$, respectively, only show a significant variation in the blue wavelength region. In the blue wavelength region the detection of the signal by the spectrophotometer is much harder and the signal to noise ratio is lower than in other wavelength regions. Furthermore the signal to noise ratio of the parameters reduces in those areas where the white substrate, the colored substrate and the colorant itself have more or less the same spectral reflectance values.

In the second experiment, we printed the test charts that were used to characterize the inks for each of the inks being considered, together with a classical test chart that consists of a set of overprints of various raster densities of the inks. Table 1 shows the comparison between the calculated colors of the overprints using the method of the invention with the measured colors of the overprints.

TABLE 1

Comparison between measured and calculated overprints.

| Ink | Num. of patches | Num. of overprints | Average ΔE | Maximum ΔE |
|---|---|---|---|---|
| MATCHPRINT ® CMYK | 25 | 2 | 2.5 | 4.1 |
| CROMALIN ® CMYK | 50 | 2 | 1.8 | 3.9 |
| CROMALIN ® PANTONE PrB/ PANTONE Gr/ PANTONE Y PANTONE K | 1331 | 3 | 3.0 | 5.3 |
| CROMALIN ® CMYK | 1331 | 3 | 2.9 | 5.1 |

In the first column lists inks considered in the experiment and the kind of printing technique used. The second column indicates the number of patches in the comparison between the colors predicted using the inventive method and those measured. The third column gives the average color differences in units of ΔE over the measured patches and predicted patch colors, and the fourth column shows the maximum deviation between the calculated and the measured samples.

Some of the inks included have a relatively strong scattering component, while others do not scatter at all. Given the limited reproducibility of the CROMALIN® (E.I. du Pont de Nemours and Company, Wilmington, Del.) and MATCHPRINT® processes, the results are excellent. Indeed, as is known to those in the art, it is pretty difficult to make any analog proof reproducible within 3 ΔE. Even the spatial uniformity of such proofing device is in many cases not better than 3 ΔE for several reasons, including the spatial variation of the ultra-violet illumination used to make th prints.

Thus a method and apparatus for characterizing colorants has been disclosed.

Note that in practicing the invention, the colorant parameters may not be explicitly determined until an overprint is required. Rather, the different measured spectra may be stored for any particular colorant. Similarly, in the case of there being interaction between the different colorant layers, only the effective parameters as required to determine the overprint may be calculated. Both of these are included in the scope of the invention, in the sense that the colorant parameters are implicitly determined. For example, the step of determining the colorant parameters is included in determining the effective colorant parameters directly from the measured spectra. In such a case, the measured spectra are themselves the colorant parameters.

In an improved practical implementation, a modified data structure is used to store the colorant parameters. Initially, the stored parameters for any colorant are the measured spectra, and a flag is set to so indicate. When calculation of the colorant parameters carried out, for example to determine an overprint which involves the overprint, the so-calculated colorant parameters are stored, and the flag is cleared in the data structure to indicate that the stored parameters are the calculated colorant parameters. This modified embodiment improves computational efficiency by only requiring the colorant parameters to be calculated once for any colorant.

In developing the preferred embodiment, Eq. (6a) and (6b) may be obtained using a simple probabilistic model of the effect of layers under and over the particular colorant layer—including that the effect on each layer j (not equal to the layer of interest i) is independent of other layers so that a simple multiplicative relationship is used. Alternate embodiments of the invention may incorporate other models, and all such interaction models are within the scope of the present invention.

Similarly, the preferred embodiment included neglecting second order changes in the ink amounts in the expression of Eqs. (6a) and (6b), and in alternate embodiments, such higher order effects may be taken into account.

Also, in the preferred embodiment, the reasonable assumption is made that the parameters are ink layer thickness dependent. Also, another assumption made is that the ink volume is approximately constant before and after any interaction between the ink layers. In alternate embodiments, on or more of these assumptions are not made, or alternate appropriate assumptions are made, leading to different mathematical expression. All such variations are included in the scope.

Also, in the preferred embodiment, the assumption was made that the parameters of the last grey overprint are not effected by the previously laid layers. An alternate would be to apply this simplifying assumption only to the determination of the modified parameters of this third grey layer, such modified parameters denoted by $\alpha'_g(\lambda)$, $\mu'_g(\lambda)$, and $S'_g(\lambda)$, and then to use these modified parameters in Eq. (15). That is, to use $$R''(l, p, \lambda) = (1 - \alpha'_g(\lambda))) * R'(l, p, \lambda)^{\mu'_g(\lambda)} + S'_g(\lambda)$$

in place of Eq. (15) above. Alternatively, one may characterize the influence of the inks below this third layer in an iterative way.

Note that the preferred embodiment described one way of obtaining a sufficient number of measurements of different amounts of the colorant on different backgrounds to determine the required number of colorant parameters: one set of four measurements on four backgrounds, followed by an overprint of these four sets, leading to another four sets of measurements. Eight set of measurements with eight different environments were thus obtained to determine the eight parameters. In one alternate embodiment applicable to the case where in any overprint, any colorant layer is unaffected by "future" colorant layers, ie., by any colorant layers laid on top of the colorant, rather than printing with four backgrounds, printing with eight backgrounds is carried out, and then no overprints are required to obtain a sufficient number of set of spectra to determine the eight colorant parameters. In yet another alternate, the initial printing is at only three backgrounds, a light, medium, and dark background, and then two overprints with a second and third colorant are carried out, leading top a total of nine possible spectra. Eight of these are sufficient to determine the colorant parameters. Thus, the general case, is that a number of sets of prints is made on a number of backgrounds, and the spectra measured. If the selected number of sets is not sufficient to determine the colorant parameters, then one or more overprints are made and spectra measured until a sufficient number of spectra is obtained to determine the colorant parameters. For example, to determine eight colorant parameters, a total of eight sets if spectra a sufficient. At least one overprinting is carried out when the effect of any "spreading" or "mixing" is to be incorporated in the parameters, that is, when the colorant layer may be affected by future layers, and such effect if to be incorporated in the colorant parameters.

Note also that the terms "determining" and "solving for" the colorant parameters from the measured spectra may include solving a set of equations, or estimating the set of parameters from the measurements, for example, in the least-squared sense, the estimating typically including carrying out an optimization (e.g., minimization) with a particular objective function (e.g., a squared error cost function).

In another alternative for obtaining the different backgrounds, set of prints are overprinted on top of each other. That is, a first set of prints is made on the substrate for a set of coverage percentages, then to obtain a second set of prints on another set backgrounds, a set of prints with a second set of coverage percentages is made to produce an intermediate set, and then a set of prints at a third set of coverage percentages is made over the intermediate set, so that the colorant is overprinted twice in the second set of prints. A third (and subsequent set of prints can be made by repeating this process. Thus, the colorant is overprinted three times in the third set of prints, and more times in subsequent sets of prints.

While the description of the preferred embodiment is for a reflective image as would occur with printing with a colorant such as a dye or pigment based ink, on a substrate type such as paper of a particular type, plastic of a particular type, fabric of a particular type, or ceramic material of a particular type, using printing techniques such as offset, gravure, flexo, ink jet or dye sublimation, the present invention is not restricted to reflective surfaces. The method and apparatus of the present technique is applicable also to determining the transmittance of colorants when such colorants are deposited on or imbedded in a transmitting or semi-transparent substrate, such as transparent or semi-transparent film, as would occur in making photographic transparencies and in printing on a transparent or semi-transparent carrier of a particular type. In such a case, rather than reflection spectra being determined and used, transmittance spectra are used. How to extend the method of the present invention to deal with transmission images would be clear to one of ordinary skill in the art.

Note that the above description was for a scattering colorant. A non scattering colorant has S and $\Delta S$ zero. Therefore, rather than print four sets of patches as shown in FIGS. 1 and 2, in the case of the colorants (inks) known not to be scattering, one may alternatively print three sets of patches, leaving out one of the first or the second grey (g1 or g2). The procedure follows the above described procedure with the simplification to the equations that S and $\Delta S$ zero.

Also note also that while the above discussion was for reflective printing, the transmittive (transparency) printing case follow in a straightforward manner and would be clear to one of ordinary skill in the art from the description for the reflective case.

Also note that in the preferred embodiment, halftone printing with a black ink was used to obtain a lightly colored (e.g., white) substrate and, and medium and darker medium colored substrates. Other embodiments may use other mechanisms for having the different backgrounds. Also, eleven patches were included for each background in the preferred embodiments. Other embodiments may include fewer or more patches, with equal or unequal increments of ink coverage. The method is not limited to halftone printing. One can apply the method to modulated printing, such as color laser printing and dye sublimation printing. In such cases, for example, instead of a p % dot percentage screen, one would print an area of p % modulated colorant intensity. The method also applies to photographic printing and transparency making, in which case colorant coverage would represent the amount of photographic colorant. How to extend the methods of the present invention to non-screened printing would be clear to those of ordinary skill in the art.

Also, while in the preferred embodiment, a spectrophotometer is used for the measurements, other instruments such as a spectroradiometers may be used. Also, as would be clear to those of ordinary skill in the art, in the case of transmission imaging, transmission spectra are measured, and any instrument capable of measuring transmission spectra may be used.

Other numerical methods, such as the method of steepest descent, etc., may also be used, and other error functions can be used with such methods.

Also clear to those of ordinary skill in the art would be that if the colorant parameters need to be determined for only a range of coverage percentages rather than for any coverage percentage, than, in another aspect of the method of the invention, the sets of prints of the colorants only would need to cover the particular range of interest of coverage percentages.

Although this invention has been described with respect to preferred embodiments, those embodiments are illustrative only. No limitation with respect to the preferred embodiments is intended or should be inferred. It will be observed that numerous variations and modifications may be effected without departing from the true spirit and scope of the novel concept of the invention, and it is intended that the scope of the invention be defined by the claims appended hereto.

What is claimed is:

1. A method for determining a set of $n_p$ parameters that spectrally characterizes a colorant in order to predict the color of an overprint of the colorant with other colorants printed in an order of printing at a set of respective coverage percentages on a substrate of a substrate type using a printing technique, the method comprising:

(a) making a selected number of sets of prints of the colorant on a selected number of respective substrates of the same substrate type, a set of prints including prints of the colorant on the respective substrate at a range of coverage percentages of interest, the selected number of prints at any particular coverage percentage being on backgrounds of said selected number of different background colors;

(b) measuring the spectra of the prints of the selected number of sets of prints and the spectra of each of the different background colors;

(c) if the selected number of sets of measured spectra is not sufficient to determine the set of $n_p$ colorant parameters of the colorant as a function of wavelength and the coverage percentage of the particular colorant, overprinting one or more of the sets of prints of the colorant one or more times with at least one overprinting colorant, and measuring the spectra of each overprinting colorant and of the overprinted prints in the overprinted set of prints until a sufficient number of different measured spectra is obtained for determining the set of $n_p$ colorant parameters; and (d) determining from the measured spectra the set of $n_p$ colorant parameters of the colorant as a function of wavelength and the coverage percentage of the particular colorant.

2. The method of claim 1, wherein the effective coverage of the colorant in the overprint is affected by at least one of the other colorants laid under the colorant in the overprint of the colorant, and wherein the set of colorant parameters of the colorant substantially incorporates the effect of the other colorants laid under the colorant in the overprint.

3. The method of claim 1, wherein the effective coverage of the colorant in the overprint is affected by at least one of the other colorants laid under or over the colorant in the overprint of the colorant, and wherein the set of colorant parameters of the colorant substantially incorporates the effect of the other colorants laid under or over the colorant in the overprint, and wherein said step (c) includes overprinting at least one set of prints at least once.

4. The method of claim 1 wherein in said step (a), the selected number of sets of prints is at least 3 for the colorant being a non-scattering colorant and at least 4 for the colorant being a scattering colorant, and wherein in said step (a), the respective substrates on which the sets of prints are made include a lightly colored substrate, a first medium colored substrate, a darkly colored substrate, and, in the case of a scattering colorant, a second medium colored substrate, wherein in said step (c), the one or more overprinting colorants are medium colored colorants, and wherein said step (d) essentially uses a relationship relating the spectrum of a print of a selected colorant at a selected coverage percentage of said range of coverage percentages on a base substrate to the spectrum of the base substrate and the set of colorant parameters of the selected colorant at the selected coverage percentage.

5. The method of claim 4 wherein the medium colored substrates are greyish substrates, and the darkly colored substrate is a blackish substrate, and the medium colored overprinting colorants are each a greyish colorant.

6. The method of claim 5, wherein the greyish colorant is a black colored colorant at a medium coverage percentage, the medium colored substrates are the lightly colored substrate printed with a black colorant at a first medium coverage percentages and at a second medium coverage percentage, and the darkly colored substrate is the lightly colored substrate printed with a black colorant at a high coverage percentage.

7. The method of claim 1 wherein in said step (a), (i) making a first set of prints comprises making a set of prints on a first substrate with a first set of coverage percentages;

(ii) making the second set of prints comprises making a set of prints with a second set of coverage percentages to produce a first intermediate set, and on the first intermediate set, making a set of prints at a third set of coverage percentages so that the colorant is overprinted twice in said second set of prints; and (iii) making the third and any subsequent sets of prints comprises repeating said step (a)(ii) iteratively so that the colorant is overprinted three times in said third set of prints, and more times in subsequent sets of prints.

8. The method of claim 1 wherein, for a particular colorant percentage not equal to any of said set of coverage percentages, said step (d) includes interpolation of the spectra to determine interpolated values of the spectra, and determining from said interpolated values the set of colorant parameters for the colorant at said particular colorant percentage.

9. The method of claim 1 wherein, for a particular colorant percentage not equal to any of said set of coverage percentages, said step (d) includes determining values of the set of colorant parameters at coverage percentages of said set of coverage percentages above and below the particular coverage percentage, and interpolating to determine the set of colorant parameters for the colorant at said particular colorant percentage.

10. A method for determining respective sets of $n_p$ parameters that spectrally characterize one or more colorants in order to predict the color of an overprint of the colorants printed in an order of printing at a set of respective coverage percentages on a substrate of a substrate type using a printing technique, each of the colorants defined by a respective recipe of one or more basic colorants, the method comprising, for any particular colorant of the colorants:

(a) for each basic colorant of the respective recipe defining the particular colorant:

(a)(i) making a selected number of sets of prints of the basic colorant on a selected number of respective substrates of the same substrate type, a set of prints comprising prints of the basic colorant on the respective substrate at a range of coverage percentages of interest, the selected number of prints at any particular coverage percentage being on backgrounds of said selected number of different background colors, (a)(ii) measuring the spectra of the prints of the selected number of sets of prints and the spectra of each of the different background colors, and (a)(iii) if the selected number of sets of measured spectra is not sufficient to determine the set of $n_p$ colorant parameters of the basic colorant as a function of wavelength and the coverage percentage of the basic colorant, overprinting one or more of the sets of prints of the basic colorant one a more times with at least one overprinting colorant, and measuring the spectra of the overprinted prints in the overprinted set of prints until a sufficient number of different measured spectra is obtained for determining the set of $n_p$ colorant parameters of the basic colorant; and (b) determining from the recipe and from the measured spectra, the set of $n_p$ colorant parameters of the particular colorant as a function of the coverage percentage and of wavelength.

11. The method of claim 10, wherein the effective coverage of the particular colorant in the overprint is affected by at least one of the other colorants laid under the particular colorant in the overprint of the colorants, and wherein the set of colorant parameters of the particular colorant substantially incorporates the effect of the other colorants laid under the colorant in the overprint.

12. The method of claim 10, wherein the effective coverage of the particular colorant in the overprint is affected by at least one of the other colorants laid under or over the colorant in the overprint of the colorant, and wherein the set of colorant parameters of the colorant substantially incorporates the effect of the other colorants laid under or over the colorant in the overprint, and wherein said step (a)(iii) includes overprinting at least one set of prints at least once.

13. The method of claim 10 wherein in said step (a), the selected number of sets of prints is at least 3 for the particular colorant being a non-scattering colorant and at least 4 for the particular colorant being a scattering colorant, and wherein in said step (a)(i), the respective substrates on which the sets of prints are made include a lightly colored substrate, a first medium colored substrate, a darkly colored substrate, and, in the case of a scattering colorant, a second medium colored substrate, wherein in said step (a)(iii), the overprinting colorants are medium colored colorants, and wherein said step (b) essentially uses a relationship relating the spectrum of a print of a selected colorant at a selected coverage percentage of said range of coverage percentages on a base substrate to the spectrum of the base substrate and the set of colorant parameters of the selected colorant at the selected coverage percentage.

14. The method of claim 13 wherein the medium colored substrates are greyish substrates, and the darkly colored substrate is a blackish substrate, and the medium colored colorants are each a greyish colorant.

15. The method of claim 14, wherein the greyish colorant is a black colored colorant at a medium coverage percentage, the medium colored substrates are the lightly colored substrate printed with a black colorant at a first medium coverage percentages and at a second medium coverage percentage, and the darkly colored substrate is the lightly colored substrate printed with a black colorant at a high coverage percentage.

16. The method of claim 12 wherein in said step (a)(i),
   (i-1) making a first set of prints comprises making a set of prints on a first substrate with a first set of coverage percentages;
   (i-2) making the second set of prints comprises making a set of prints with a second set of coverage percentages to produce a first intermediate set, and on the first intermediate set, making a set of prints at a third set of coverage percentages so that the colorant is overprinted twice in said second set of prints; and
   (i-3) making the third and any subsequent sets of prints comprises repeating said step (i-2) iteratively so that the colorant is overprinted three times in said third set of prints, and more times in subsequent sets of prints.

17. The method of claim 10 wherein, for a particular colorant percentage not equal to any of said set of coverage percentages, said step (b) includes interpolation of the spectra to determine interpolated values of the spectra, and determining from said interpolated values the set of colorant parameters for the particular colorant at said particular colorant percentage.

18. The method of claim 10 wherein, for a particular colorant percentage not equal to any of said set of coverage percentages, said step (b) includes determining values of the set of colorant parameters at coverage percentages of said set of coverage percentages above and below the particular coverage percentage, and interpolating to determine the set of colorant parameters for the particular colorant at said particular colorant percentage.

19. The method of claim 10 wherein the method further includes:
   making a set of dilutions of each basic colorant in the recipe; and
   repeating said step (a) for each dilution of each said basic colorant, and wherein said step (b) includes, using said recipe and the measured spectra from the repeating of said steps (a), calculating a set of calculated spectra that would result by producing new sets of prints, each new set comprising prints of the colorant at the range of coverage percentages on the respective substrates, the print at any particular coverage percentage being on backgrounds of said selected number of different background colors.

20. The method of claim 19, wherein for the particular colorant, each said basic colorant has a corresponding concentration in said recipe and wherein said step (b) further comprises determining for each basic colorant from at least some of the spectra measured in said steps (a)(ii) and (iii), the Kubelka-Munk coefficient values of said each basic colorant at the corresponding concentration.

21. The method of claim 20, wherein for any basic colorant whose corresponding concentration is not one of said dilutions, said determining the Kubelka-Munk coefficient values includes determining the Kubelka-Munk coefficient values for at least two of said dilutions, and interpolating between the so determined Kubelka-Munk coefficient values for the at least two of said dilutions.

22. The method of claim 19 wherein in said step (a), the selected number of sets of prints is at least 3 for the particular colorant being a non-scattering colorant and at least 4 for the particular colorant being a scattering colorant, and wherein in said step (a), the respective substrates on which the sets of prints are made include a lightly colored substrate, a first medium colored substrate, a darkly colored substrate, and, in the case of a scattering colorant, a second medium colored substrate, wherein in said step (a), the overprinting colorants are medium colored colorants, and wherein said step (b) essentially uses a relationship relating the spectrum of a print of a selected colorant at a selected coverage percentage of said range of coverage percentages on a base substrate to the spectrum of the base substrate and the set of colorant parameters of the selected colorant at the selected coverage percentage.

23. The method of claim 10 further comprising the step of
   determining the color spectrum of an overprint of the colorants printed at the set of respective percentages, including, for each colorant, in the order of the overprinting, recursively calculating the spectrum of the overprint on a selected base substrate using the parameters of said each colorant and the spectrum of the selected base substrate, the selected base substrate for the first printed colorant being the substrate, and the selected base substrate for each successive overprint being the overprint of all the previously printed colorants on the substrate, such selected base substrate for each successive overprint having the spectrum calculated in the previous recursion.

24. The method of claim 10 further comprising the steps of
   determining a set of effective parameters for any colorant whose effective coverage percentage is affected by at least one of the colorant parameters, said set of effective parameters determined by the respective coverage percentages of any other colorants laid over or under the particular colorant; and determining the color spectrum of an overprint of the colorants printed at the set of respective percentages, including, for each colorant, in the order of the overprinting, recursively calculating the spectrum of the overprint on a selected base substrate using the effective parameters of said each colorant and the spectrum of the selected base substrate, the selected base substrate for the first printed colorant being the substrate, and the selected base substrate for each successive overprint being the overprint of all the previously printed colorants on the substrate, such selected base substrate for each successive overprint having the spectrum calculated in the previous recursion, the effective parameter of any colorant whose effective coverage percentage is unaffected by the coverage percentages of any of the other colorants being the respective parameter of the colorant in the set of colorant parameters.

25. The method of claim 24 further including converting the color spectrum of the overprint of the colorants to a set of color values which describe the color appearance overprint of the colorants.

26. The method of claim 25 further including using said color values to drive a display.

27. The method of claim 25 wherein said color values are the device dependent color values for creating said appearance on a printing device.

28. The method of claim 10 wherein the overprint is of a pixel of an image.

29. The method of claim 23 wherein the overprint is of a pixel of an image and determining the overprint is repeated for all pixels in the image.

30. A method of accurately predicting the color of an overprint of a set of colorants on a substrate at a respective set of coverage percentages, the method comprising:
(a) characterizing each colorant with a set of colorant parameters determined at the coverage percentage of the colorant in the overprint; and
(b) calculating the color of the overprint using the colorant parameters and the color of the substrate,
said characterizing not requiring measurement of colors of overprints of the colorants,
wherein said characterizing step (a) includes determining a sets of $n_p$ parameters for each of the colorants, the set of parameters spectrally characterize the colorant, each of the colorants defined by a respective recipe of one or more basic colorants, said characterizing step (a) further comprising, for any particular colorant of the colorants:
(a)(i) for each basic colorant of the respective recipe defining the particular colorant:
making a selected number of sets of prints of the basic colorant on said selected number of respective substrates of the same substrate type, a set of prints comprising prints of the basic colorant on the respective substrate at a range of coverage percentages of interest, the selected number of prints at any particular coverage percentage being on backgrounds of said selected number of different background colors, and
measuring the spectra of the prints of the selected number of sets of prints and the spectra of each of the different background colors;

if the selected number of sets of measured spectra is not sufficient to determine the set of $n_p$ colorant parameters of the basic colorant as a function of wavelength and the coverage percentage of the basic colorant, overprinting one or more of the sets of prints of the basic colorant one a more times with at least one overprinting colorant, and measuring the spectra of the overprinted prints in the overprinted set of prints until a sufficient number of different measured spectra is obtained for determining the set of $n_p$ colorant parameters of the basic colorant; and (a)(ii) determining from the recipe and from the measured spectra, the set of $n_p$ colorant parameters of the particular colorant as a function of the coverage percentage and of wavelength.

31. A method of accurately predicting the color of an overprint of a set of colorants on a substrate at a respective set of coverage percentages, the method comprising:
(a) characterizing each colorant with a set of colorant parameters determined at the coverage percentage of the colorant in the overprint; and
(b) calculating the color of the overprint using the colorant parameters and the color of the substrate,
said characterizing not requiring measurement of colors of overprints of the colorants,
wherein said step (b) of calculating comprises:
determining the color spectrum of the overprint of the colorants printed at the set of respective percentages, including, for each colorant, in the order of the overprinting, recursively calculating the spectrum of the overprint on a selected base substrate using the parameters of said each colorant and the spectrum of the selected base substrate, the selected base substrate for the first printed colorant being the substrate, and the selected base substrate for each successive overprint being the overprint of all the previously printed colorants on the substrate, such selected base substrate for each successive overprint having the spectrum calculated in the previous recursion.

32. A method of accurately predicting the color of an overprint of a set of colorants on a substrate at a respective set of coverage percentages, the method comprising:
(a) characterizing each colorant with a set of colorant parameters determined at the coverage percentage of the colorant in the overprint; and
(b) calculating the color of the overprint using the colorant parameters and the color of the substrate,
said characterizing not requiring measurement of colors of overprints of the colorants,
wherein the effective coverage of at least one particular colorant in the overprint is affected by at least one of the other colorants laid over or under the particular colorant in the overprint of the colorants, and wherein the set of colorant parameters of the particular colorant substantially incorporates the effect of the other colorants laid over or under the colorant in the overprint, the method further comprising:
determining a set of effective parameters for any colorant whose effective coverage percentage is affected by at least one of the colorant parameters, said set of effective parameters determined by the respective coverage percentages of any other colorants laid over or under the particular colorant, determining the color spectrum of the overprint of the colorants printed at the set of respective percentages, including, for each colorant, in the order of the overprinting, recursively calculating the spectrum of the overprint on a selected base substrate using the effective parameters of said each colorant and the spectrum of the selected base substrate, the selected base substrate for the first printed colorant being the substrate, and the selected base substrate for each successive overprint being the overprint of all the previously printed colorants on the substrate, such selected base substrate for each successive overprint having the spectrum calculated in the previous recursion, the effective parameters of any colorant whose effective coverage percentage is unaffected by the coverage percentages of any of the other colorants being the parameter of the colorant.

33. A method of accurately predicting the color of an overprint of a set of colorants on a substrate at a respective set of coverage percentages, the method comprising:

(a) characterizing each colorant with a set of colorant parameters determined at the coverage percentage of the colorant in the overprint; and (b) calculating the color of the overprint using the colorant parameters and the color of the substrate, said characterizing not requiring measurement of colors of overprints of the colorants, wherein the overprint is of a pixel of an image and wherein predicting the color of the overprint is repeated for all pixels in the image.

34. An apparatus for determining the color of an overprint of one or more colorants each colorant printed in an order at a respective coverage percentage on a substrate of a substrate type, each colorant defined by a set of $n_p$ colorant parameters for the coverage percentage the colorant is printed on for the substrate type the colorant is printed on, $n_p$ being at least 2 for a non-scattering colorant and at least 3 for a scattering colorant, the set of colorant parameters defined by a relationship relating the spectrum of a print of a selected colorant at a selected coverage percentage on a base substrate to the spectrum of the base substrate and the set of colorant parameters of the selected colorant at the selected coverage percentage, the apparatus comprising:

(a) a first memory for storing a spectrum, said first memory initially storing the spectrum of the substrate;

(b) a logic unit, the logic unit including a set of one or more inputs, the inputs coupled to signals specifying a coverage percentage, a second memory for storing the values of the colorant parameters of at least one of the colorants at a selected set of coverage percentages, a set of one or more multidimensional outputs, each multidimensional output generating the values of the colorant parameters at the coverage percentage of a respective input of the set of inputs, (c) a combiner unit having a first input coupled to the first memory, the combiner unit coupled to said set of outputs of the logic unit for determining as an output the spectrum of an overprint essentially according to the relationship.

* * * * *

UNITED STATES PATENT AND TRADEMARK OFFICE
CERTIFICATE OF CORRECTION

PATENT NO. : 6,483,607 B1
DATED : November 19, 2002
INVENTOR(S) : Van de Capelle et al.

It is certified that error appears in the above-identified patent and that said Letters Patent is hereby corrected as shown below:

<u>Title page,</u>
Item [73], Assignee, change "Detrix, N. V., Wijnaarde" to -- Dotrix, N. V., Zwijnaarde (BE) --

Signed and Sealed this

Eighteenth Day of March, 2003

JAMES E. ROGAN
*Director of the United States Patent and Trademark Office*